(12) United States Patent
Burton et al.

(10) Patent No.: US 7,205,124 B1
(45) Date of Patent: Apr. 17, 2007

(54) UTROPHIN GENE PROMOTER

(75) Inventors: Edward Burton, Pittsburgh, PA (US); Jonathan Tinsley, Oxford (GB); Kay Davies, Oxford (GB)

(73) Assignee: Isis Innovation Limited, Oxford (GB)

( * ) Notice: Subject to any disclaimer, the term of this patent is extended or adjusted under 35 U.S.C. 154(b) by 563 days.

(21) Appl. No.: 10/089,928

(22) PCT Filed: Oct. 4, 2000

(86) PCT No.: PCT/GB00/03800

§ 371 (c)(1),
(2), (4) Date: Aug. 27, 2002

(87) PCT Pub. No.: WO01/25461

PCT Pub. Date: Apr. 12, 2001

(30) Foreign Application Priority Data

Oct. 4, 1999 (GB) .................................. 9923423.9

(51) Int. Cl.
*C12P 21/02* (2006.01)
(52) U.S. Cl. ............. 435/69.1; 435/320.1; 435/252.33; 435/471; 536/24.1
(58) Field of Classification Search .................... None
See application file for complete search history.

(56) References Cited

U.S. PATENT DOCUMENTS 5,972,609 A * 10/1999 Tinsley et al. ................. 435/6

FOREIGN PATENT DOCUMENTS

| EP | 1 033 401 A2 | 9/2000 |
| WO | WO96/34101 | * 10/1996 |
| WO | WO 97/22696 | 6/1997 |

OTHER PUBLICATIONS

Tubby, B; XP-002160374; Database EMBL Online; Sequence HS91J24, Human DNA Sequence from Clone 91J24 on Chromosome 6q24.

A. et al; A second promoter provides an alternative target for therapeutic up-regulation of utrophin in Duchenne muscular dystrophy; *PNAS*; vol. 96; No. 24; Nov. 1999; 14025-14030.

Man, Nguyen et al. Full-length and short forms of utrophin, the dystrophin-related protein; *FEBS Letters*; Jan. 1995; vol. 358 No. 3; Amsterdam, NL.

* cited by examiner

*Primary Examiner*—James Ketter
(74) *Attorney, Agent, or Firm*—Fulbright & Jaworski LLP

(57) ABSTRACT

Second promoter for mouse and human utrophin genes. The promoters or fragments and derivatives may be used to control transcription of heterologous sequences, including coding sequences of reporter genes. Expression systems such as host cells containing nucleic acid constructs which comprise a promoter as provided operably linked to a heterologous sequence may be used to screen substances for ability to modulate activity of the utrophin promoter. Substances with such ability may be manufactured and/or used in the preparation of compositions such as medicaments. Up-regulation of utrophin expression may compensate for dystrophin loss in muscular dystrophy patients.

33 Claims, 15 Drawing Sheets

```
                                                                                                                    Alu Sq 86% identity
                                                                                                 NdeI
500 tttctattccacaacaagcaagaaaagaatgatgagaaggactagaaagtatgatcatgattttccttgctttcgatgtggtggacacatgcaagaagtgacagcaggagtcgagacaggaccaacaa 649

CA repeat                                                                       Alu Sq 83% identity
650 tggtgaaatcccgtctctactaaacacacacacacacacacacacacacacacacacaatagccggcatgtgtgggcacctgtaatcccagctactgggaggctgaggcacagaatgacttgaaccaggagg 799

IL6-RE
    cgaggtgcagtgagctgagatcatgccattgcactccagcctgggtgacgagtgaaaatgatgataaagagagcaggtgaccacaaagagaataggctggaaaattgtctaaatggtggcctcttctctattagct 949
800

NdeI             EcoR1
950 gcatatggtcaagtttattttccccagtagcgaattctaaggatgaagaaatcctttcagtttacttcccaaggtgtataactactactagtgaataataagtccaattttattcttgaagtatagtaatatgtaacg 1099

1100 aaactcctaaggccagtgtataccccaggcaaacgccttctaacatctttattactctacgcagtgggtaggaggtgggtggagtgcccctcccagctgatctgtcaaaacaggaagcaagttataatctgtcatag   gaa 1246 silencer/CdxA                              c-ets1/PEA3/XrpF1            Sp1              Ap1
1247 catgaatagaggccctagttgtgactattaaaaaacaaaaaacctgctaaggagtttcactgactaactcccctctggtgtttagaggaggtgggtaggttagtcagatccctctcatggaaaataaagcc 1396
                                                                                   CACbp cap                                M     S   G     L    A     A    T    T    F
1397 accaaaaaaaaaaaaaaacccaaattaacacacaggacatCCCAGTGTGCAGTTCGAAGGCTGCTTTTGTTGTCCCACTTCCTCCACATCTTTTCCTCATCATCTAAGCAGATGTAGGTGATGAGGCGGCCTGCTGCAGCCACCACGTTT 1546
                                                                       initiator H    W    K    K    C    R     L    D    L    P    G    H    V    A    L    Q    A    C    K    R    L    P    D
1547 CATTGGAAAAAGTGCAGATTGGATTTGCCAGGCTCTCCAGGCATGGCATGCCAAGCGATTACCAGgtagtttgtcaacttgcactgactcccagtcagtgagtttcttaagaaacgtctatgaagaacaggtcttcattcagtt 1696
                                                                              splice donor
```

A.
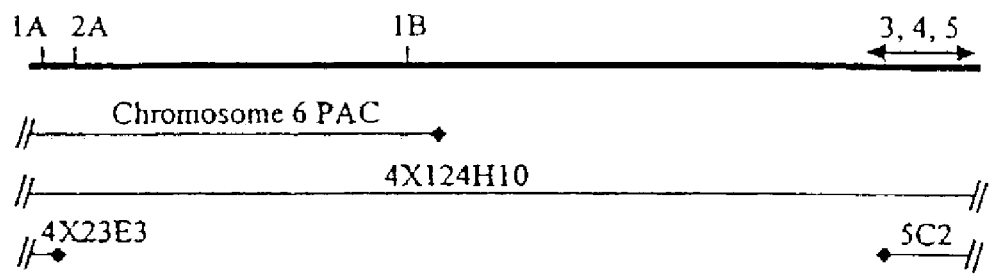
B.
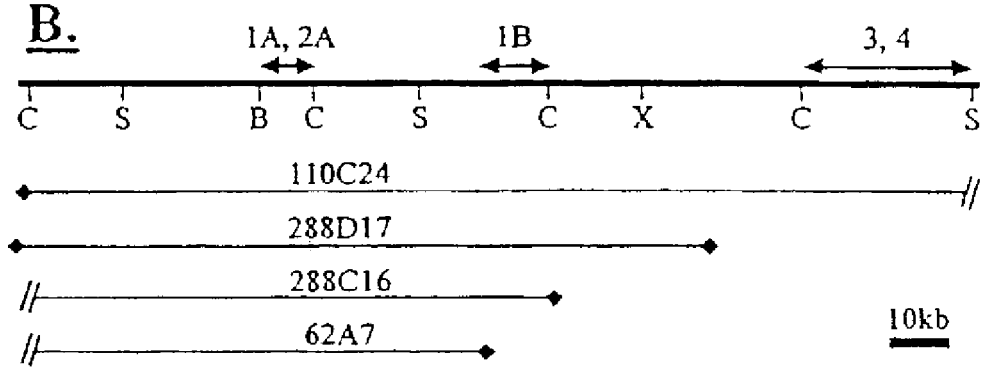
C.
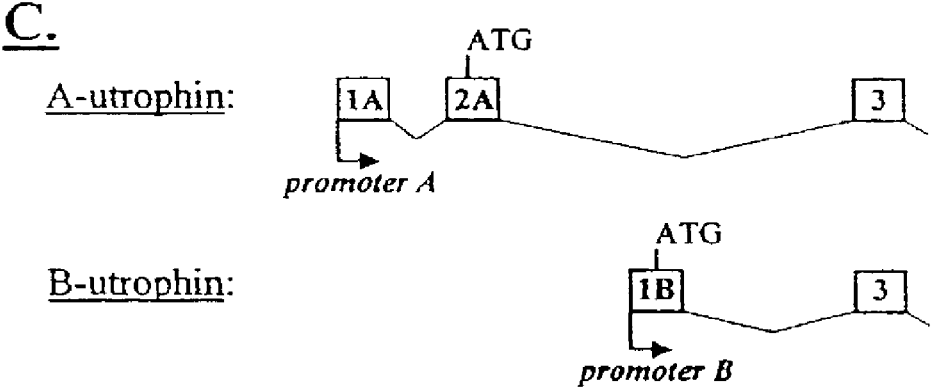
Figure 5

Human B-utrophin up to nucleotide 1500, deduced translation

```
          CCCAGTGTGCAGTTCGAAGGCTGCTTTTGTTGTCCACTTCCTCCACATCTTTTTCCTCAT
    1     ---------+---------+---------+---------+---------+---------+  60
          GGGTCACACGTCAAGCTTCCGACGAAAACAACAGGTGAAGGAGGTGTAGAAAAAGGAGTA

CATCTAAGCAGATGTAGGTGATGAGCGGCCTGGCAGCCACCACGTTTCATTGGAAAAAGT
    61    ---------+---------+---------+---------+---------+---------+  120
          GTAGATTCGTCTACATCCACTACTCGCCGGACCGTCGGTGGTGCAAAGTAACCTTTTTCA

M  S  G  L  A  A  T  T  F  H  W  K  K  C  -
                                                      Exon 1B ◄──┬──► Exon 3
          GCAGATTGGATTTGCCAGGGCATGTAGCTCTCCAGGCTTGCAAGCGATTACCAG|ATGAAC
    121   ---------+---------+---------+---------+---------+----|----+  180
          CGTCTAACCTAAACGGTCCCGTACATCGAGAGGTCCGAACGTTCGCTAATGGTC|TACTTG c    R  L  D  L  P  G  H  V  A  L  Q  A  C  K  R  L  P  D  E  H  -

ACAATGACGTACAGAAGAAAACCTTTACCAAATGGATAAATGCTCGATTTTCAAAGAGTG
    181   ---------+---------+---------+---------+---------+---------+  240
          TGTTACTGCATGTCTTCTTTTGGAAATGGTTTACCTATTTACGAGCTAAAAGTTTCTCAC c    N  D  V  Q  K  K  T  F  T  K  W  I  N  A  R  F  S  K  S  G  -

GGAAACCACCCATCAATGATATGTTCACAGACCTCAAAGATGGAAGGAAGCTATTGGATC
    241   ---------+---------+---------+---------+---------+---------+  300
          CCTTTGGTGGGTAGTTACTATACAAGTGTCTGGAGTTTCTACCTTCCTTCGATAACCTAG c    K  P  P  I  N  D  M  F  T  D  L  K  D  G  R  K  L  L  D  L  -

TTCTAGAAGGCCTCACAGGAACATCACTGCCAAAGGAACGTGGTTCCACAAGGGTACATG
    301   ---------+---------+---------+---------+---------+---------+  360
          AAGATCTTCCGGAGTGTCCTTGTAGTGACGGTTTCCTTGCACCAAGGTGTTCCCATGTAC c    L  E  G  L  T  G  T  S  L  P  K  E  R  G  S  T  R  V  H  A  -

CCTTAAATAACGTCAACAGAGTGCTGCAGGTTTTACATCAGAACAATGTGGAATTAGTGA
    361   ---------+---------+---------+---------+---------+---------+  420
          GGAATTTATTGCAGTTGTCTCACGACGTCCAAAATGTAGTCTTGTTACACCTTAATCACT c    L  N  N  V  N  R  V  L  Q  V  L  H  Q  N  N  V  E  L  V  N  -

ATATAGGGGGAACTGACATTGTGGATGGAAATCACAAACTGACTTTGGGGTTACTTTGGA
    421   ---------+---------+---------+---------+---------+---------+  480
          TATATCCCCCTTGACTGTAACACCTACCTTTAGTGTTTGACTGAAACCCCAATGAAACCT c    I  G  G  T  D  I  V  D  G  N  H  K  L  T  L  G  L  L  W  S  -

GCATCATTTTGCACTGGCAGGTGAAAGATGTCATGAAGGATGTCATGTCGGACCTGCAGC
    481   ---------+---------+---------+---------+---------+---------+  540
          CGTAGTAAAACGTGACCGTCCACTTTCTACAGTACTTCCTACAGTACAGCCTGGACGTCG c    I  I  L  H  W  Q  V  K  D  V  M  K  D  V  M  S  D  L  Q  Q  -

AGACGAACAGTGAGAAGATCCTGCTCAGCTGGGTGCGTCAGACCACCAGGCCCTACAGCC
    541   ---------+---------+---------+---------+---------+---------+  600
          TCTGCTTGTCACTCTTCTAGGACGAGTCGACCCACGCAGTCTGGTGGTCCGGGATGTCGG c    T  N  S  E  K  I  L  L  S  W  V  R  Q  T  T  R  P  Y  S  Q  -

AAGTCAACGTCCTCAACTTCACCACCAGCTGGACAGATGGACTCGCCTTTAATGCTGTCC
    601   ---------+---------+---------+---------+---------+---------+  660
          TTCAGTTGCAGGAGTTGAAGTGGTGGTCGACCTGTCTACCTGAGCGGAAATTACGACAGG c    V  N  V  L  N  F  T  T  S  W  T  D  G  L  A  F  N  A  V  L  -

TCCACCGACATAAACCTGATCTCTTCAGCTGGGATAAAGTTGTCAAAATGTCACCAATTG
    661   ---------+---------+---------+---------+---------+---------+  720
          AGGTGGCTGTATTTGGACTAGAGAAGTCGACCCTATTTCAACAGTTTTACAGTGGTTAAC c    H  R  H  K  P  D  L  F  S  W  D  K  V  V  K  M  S  P  I  E  -
```

Figure 8

```
                AGAGACTTGAACATGCCTTCAGCAAGGCTCAAACTTATTTGGGAATTGAAAAGCTGTTAG
        721     ---------+---------+---------+---------+---------+---------+   780
                TCTCTGAACTTGTACGGAAGTCGTTCCGAGTTTGAATAAACCCTTAACTTTTCGACAATC c              R  L  E  H  A  F  S  K  A  Q  T  Y  L  G  I  E  K  L  L  D  -

ATCCTGAAGATGTTGCCGTTCGGCTTCCTGACAAGAAATCCATAATTATGTATTTAACAT
        781     ---------+---------+---------+---------+---------+---------+   840
                TAGGACTTCTACAACGGCAAGCCGAAGGACTGTTCTTTAGGTATTAATACATAAATTGTA c              P  E  D  V  A  V  R  L  P  D  K  K  S  I  I  M  Y  L  T  S  -

CTTTGTTTGAGGTGCTACCTCAGCAAGTCACCATAGACGCCATCCGTGAGGTAGAGACAC
        841     ---------+---------+---------+---------+---------+---------+   900
                GAAACAAACTCCACGATGGAGTCGTTCAGTGGTATCTGCGGTAGGCACTCCATCTCTGTG c              L  F  E  V  L  P  Q  Q  V  T  I  D  A  I  R  E  V  E  T  L  -

TCCCAAGGAAATATAAAAAAGAATGTGAAGAAGAGGCAATTAATATACAGAGTACAGCGC
        901     ---------+---------+---------+---------+---------+---------+   960
                AGGGTTCCTTTATATTTTTTCTTACACTTCTTCTCCGTTAATTATATGTCTCATGTCGCG c              P  R  K  Y  K  K  E  C  E  E  E  A  I  N  I  Q  S  T  A  P  -

CTGAGGAGGAGCATGAGAGTCCCCGAGCTGAAACTCCCAGCACTGTCACTGAGGTCGACA
        961     ---------+---------+---------+---------+---------+---------+  1020
                GACTCCTCCTCGTACTCTCAGGGGCTCGACTTTGAGGGTCGTGACAGTGACTCCAGCTGT c              E  E  E  H  E  S  P  R  A  E  T  P  S  T  V  T  E  V  D  M  -

TGGATCTGGACAGCTATCAGATTGCGTTGGAGGAAGTGCTGACCTGGTTGCTTTCTGCTG
       1021     ---------+---------+---------+---------+---------+---------+  1080
                ACCTAGACCTGTCGATAGTCTAACGCAACCTCCTTCACGACTGGACCAACGAAAGACGAC c              D  L  D  S  Y  Q  I  A  L  E  E  V  L  T  W  L  L  S  A  E  -

AGGACACTTTCCAGGAGCAGGATGATATTTCTGATGATGTTGAAGAAGTCAAAGACCAGT
       1081     ---------+---------+---------+---------+---------+---------+  1140
                TCCTGTGAAAGGTCCTCGTCCTACTATAAAGACTACTACAACTTCTTCAGTTTCTGGTCA c              D  T  F  Q  E  Q  D  D  I  S  D  D  V  E  E  V  K  D  Q  F  -

TTGCAACCCATGAAGCTTTTATGATGGAACTGACTGCACACCAGAGCAGTGTGGGCAGCG
       1141     ---------+---------+---------+---------+---------+---------+  1200
                AACGTTGGGTACTTCGAAAATACTACCTTGACTGACGTGTGGTCTCGTCACACCCGTCGC c              A  T  H  E  A  F  M  M  E  L  T  A  H  Q  S  S  V  G  S  V  -

TCCTGCAGGCAGGCAACCAACTGATAACACAAGGAACTCTGTCAGACGAAGAAGAATTTG
       1201     ---------+---------+---------+---------+---------+---------+  1260
                AGGACGTCCGTCCGTTGGTTGACTATTGTGTTCCTTGAGACAGTCTGCTTCTTCTTAAAC c              L  Q  A  G  N  Q  L  I  T  Q  G  T  L  S  D  E  E  E  F  E  -

AGATTCAGGAACAGATGACCCTGCTGAATGCTAGATGGGAGGCTCTTAGGGTGGAGAGTA
       1261     ---------+---------+---------+---------+---------+---------+  1320
                TCTAAGTCCTTGTCTACTGGGACGACTTACGATCTACCCTCCGAGAATCCCACCTCTCAT c              I  Q  E  Q  M  T  L  L  N  A  R  W  E  A  L  R  V  E  S  M  -

TGGACAGACAGTCCCGGCTGCACGATGTGCTGATGGAACTGCAGAAGAAGCAACTGCAGC
       1321     ---------+---------+---------+---------+---------+---------+  1380
                ACCTGTCTGTCAGGGCCGACGTGCTACACGACTACCTTGACGTCTTCTTCGTTGACGTCG c              D  R  Q  S  R  L  H  D  V  L  M  E  L  Q  K  K  Q  L  Q  Q  -

AGCTCTCCGCCTGGTTAACACTCACAGAGGAGCGCATTCAGAAGATGGAAACTTGCCCCC
       1381     ---------+---------+---------+---------+---------+---------+  1440
                TCGAGAGGCGGACCAATTGTGAGTGTCTCCTCGCGTAAGTCTTCTACCTTTGAACGGGGG c              L  S  A  W  L  T  L  T  E  E  R  I  Q  K  M  E  T  C  P  L  -

TGGATGATGATGTAAAATCTCTACAAAAGCTGCTAGAAGAACATAAAAGTTTGCAAAGTG
       1441     ---------+---------+---------+---------+---------+---------+  1500
                ACCTACTACTACATTTTAGAGATGTTTTCGACGATCTTCTTGTATTTTCAAACGTTTCAC c              D  D  D  V  K  S  L  Q  K  L  L  E  E  H  K  S  L  Q  S  D  -
```

Figure 8 cont ...

Sequence Range: 1 to 6059

```
            10         20         30         40         50         60         70         80
     ACTAGTCAAG ATGAGCGGCC TGGCAGCCAC CACGTTTCAT TGGAAAAAGT GCAGATTGGA TTTGCCAGGG CATGTAGCTC
                M  S  G   L  A  A  T   T  F  H   W  K  K   C  R  L  D   L  P  G    H  V  A>

90        100        110        120        130        140        150        160
     TCCAGGCTTG CAAGCGATTA CCAGATGAAC ACAATGATGT ACAGAAGAAA ACCTTTACCA AATGGATAAA CGCTCGATTT
     L  Q  A  C  K  R  L   P  D  E   H  N  D  V   Q  K  K   T  F  T   K  W  I  N   A  R  F>

170        180        190        200        210        220        230        240
     TCCAAGAGTG GGAAACCACC CATCAGTGAT ATGTTCTCAG ACCTCAAAGA TGGGAGAAAG CTCTTGGATC TTCTCGAAGG
     S  K  S   G  K  P  P   I  S  D   M  F  S   D  L  K  D   G  R  K   L  L  D   L  L  E  G>

250        260        270        280        290        300        310        320
     CCTCACAGGA ACATCATTGC CAAAGGAACG TGGTTCCACA AGGGTGCATG CCTTAAACAA TGTCAACCGA GTGCTACAGG
     L  T  G   T  S  L   P  K  E  R   G  S  T   R  V  H   A  L  N  N   V  N  R   V  L  Q>

330        340        350        360        370        380        390        400
     TTTTACATCA GAACAATGTG GACTTGGTGA ATATTGGAGG CACGGACATT GTGGCTGGAA ATCCCAAGCT GACTTTAGGG
     V  L  H  Q  N  N  V   D  L  V   N  I  G  G   T  D  I   V  A  G   N  P  K  L   T  L  G>

410        420        430        440        450        460        470        480
     TTACTCTGGA GCATCATTCT GCACTGGCAG GTGAAGGATG TCATGAAAGA TATCATGTCA GACCTGCAGC AGACAAACAG
     L  L  W   S  I  I  L   H  W  Q   V  K  D   V  M  K  D   I  M  S   D  L  Q   Q  T  N  S>

490        500        510        520        530        540        550        560
     CGAGAAGATC CTGCTGAGCT GGGTGCGGCA GACCACCAGG CCCTACAGTC AAGTCAACGT CCTCAACTTC ACCACCAGCT
     E  K  I   L  L  S   W  V  R  Q   T  T  R   P  Y  S   Q  V  N  V   L  N  F   T  T  S>

570        580        590        600        610        620        630        640
     GGACCGATGG ACTCGCGTTC AACGCCGTGC TCCACCGGCA CAAACCAGAT CTCTTCGACT GGGACGAGAT GGTCAAAATG
     W  T  D  G   L  A  F   N  A  V   L  H  R  H   K  P  D   L  F  D   W  D  E  M   V  K  M>

650        660        670        680        690        700        710        720
     TCCCCAATTG AGAGACTTGA CCATGCTTTT GACAAGGCCC ACACTTCTTT GGGAATTGAA AAGCTCCTAA GTCCTGAAAC
     S  P  I   E  R  L  D   H  A  F   D  K  A   H  T  S  L   G  I  E   K  L  L   S  P  E  T>

730        740        750        760        770        780        790        800
     TGTTGCTGTG CATCTCCCTG ACAAGAAATC CATAATTATG TATTTAACGT CTCTGTTTGA GGTGCTTCCT CAGCAAGTCA
     V  A  V   H  L  P   D  K  K  S   I  I  M   Y  L  T   S  L  F  E   V  L  P   Q  Q  V>

810        820        830        840        850        860        870        880
     CGATAGATGC CATCCGAGAG GTGGAGACTC TCCCAAGGAA GTATAAGAAA GAATGTGAAG AGGAAGAAAT TCATATCCAG
     T  I  D  A   I  R  E   V  E  T   L  P  R  K   Y  K  K   E  C  E   E  E  E  I   H  I  Q>

890        900        910        920        930        940        950        960
     AGTGCAGTGC TGGCAGAGGA AGGCCAGAGT CCCCGAGCTG AGACCCCTAG CACCGTCACT GAAGTGGACA TGGATTTGGA
     S  A  V   L  A  E  E   G  Q  S   P  R  A   E  T  P  S   T  V  T   E  V  D   M  D  L  D>

970        980        990       1000       1010       1020       1030       1040
     CAGCTACCAG ATAGCGCTAG AGGAAGTGCT GACGTGGCTG CTGTCCGCGG AGGACACGTT CCAGGAGCAA CATGACATTT
     S  Y  Q   I  A  L   E  E  V  L   T  W  L   L  S  A   E  D  T  F   Q  E  Q   H  D  I>

1050       1060       1070       1080       1090       1100       1110       1120
     CTGATGATGT CGAAGAAGTC AAAGAGCAGT TTGCTACCCA TGAAACTTTT ATGATGGAGC TGACAGCACA CCAGAGCAGC
     S  D  D  V   E  E  V   K  E  Q   F  A  T  H   E  T  F   M  M  E   L  T  A  H   Q  S  S>

1130       1140       1150       1160       1170       1180       1190       1200
     GTGGGGAGCG TCCTGCAGGC TGGCAACCAG CTGATGACAC AAGGGACTCT GTCCAGAGAG GAGGAGTTTG AGATCCAGGA
     V  G  S   V  L  Q  A   G  N  Q   L  M  T   Q  G  T  L   S  R  E   E  E  F   E  I  Q  E>

1210       1220       1230       1240       1250       1260       1270       1280
     ACAGATGACC TTGCTGAATG CAAGGTGGGA GGCGCTCCGG GTGGAGAGCA TGGAGAGGCA GTCCCGGCTG CACGACGCTC
     Q  M  T   L  L  N   A  R  W  E   A  L  R   V  E  S   M  E  R  Q   S  R  L   H  D  A>

1290       1300       1310       1320       1330       1340       1350       1360
     TGATGGAGCT GCAGAAGAAA CAGCTGCAGC AGCTCTCAAG CTGGCTGGCC CTCACAGAAG AGCGCATTCA GAAGATGGAG
```

Figure 9

```
         L  M  E  L     Q  K  K     Q  L  Q     Q  L  S  S     W  L  A     L  T  E     E  R  I  Q     K  M  E>
       1370        1380        1390        1400        1410        1420        1430        1440
AGCCTCCCGC TGGGTGATGA CCTGCCCTCC CTGCAGAAGC TGCTTCAAGA ACATAAAAGT TTGCAAAATG ACCTTGAAGC
 S  L  P     L  G  D  D     L  P  S     L  Q  K     L  L  Q  E     H  K  S     L  Q  N     D  L  E  A>
       1450        1460        1470        1480        1490        1500        1510        1520
TGAACAGGTG AAGGTAAATT CCTTAACTCA CATGGTGGTG ATTGTGGATG AAAACAGTGG GGAGAGTGCC ACAGCTCTTC
 E  Q  V     K  V  N     S  L  T  H     M  V  V     I  V  D  E  N  S  G     E  S  A     T  A  L>
       1530        1540        1550        1560        1570        1580        1590        1600
TGGAAGATCA GTTACAGAAA CTGGGTGAGC GCTGGACAGC TGTATGCCGC TGGACTGAAG AACGTTGGAA CAGGTTGCAA
 L  E  D  Q     L  Q  K     L  G  E     R  W  T  A     V  C  R     W  T  E     E  R  W  N     R  L  Q>
       1610        1620        1630        1640        1650        1660        1670        1680
GAAATCAGTA TTCTGTGGCA GGAATTATTG GAAGAGCAGT GTCTGTTGGA GGCTTGGCTC ACCGAAAAGG AAGAGGCTTT
 E  I  S     I  L  W  Q     E  L  L     E  E  Q     C  L  L  E     A  W  L     T  E  K     E  E  A  L>
       1690        1700        1710        1720        1730        1740        1750        1760
GGATAAAGTT CAAACCAGCA ACTTTAAAGA CCAGAAGGAA CTAAGTGTCA GTGTCCGGCG TCTGGCTATA TTGAAGGAAG
 D  K  V     Q  T  S     N  F  K  D     Q  K  E     L  S  V     S  V  R  R     L  A  I     L  K  E>
       1770        1780        1790        1800        1810        1820        1830        1840
ACATGGAAAT GAAGAGGCAG ACTCTGGATC AACTGAGTGA GATTGGCCAG GATGTGGGCC AATTACTCAG TAATCCCAAG
 D  M  E  M     K  R  Q     T  L  D     Q  L  S  E     I  G  Q     D  V  G     Q  L  L  S     N  P  K>
       1850        1860        1870        1880        1890        1900        1910        1920
GCATCTAAGA AGATGAACAG TGACTCTGAG GAGCTAACAC AGAGATGGGA TTCTCTGGTT CAGAGACTCG AAGACTCTTC
 A  S  K     K  M  N  S     D  S  E     E  L  T     Q  R  W  D     S  L  V     Q  R  L     E  D  S  S>
       1930        1940        1950        1960        1970        1980        1990        2000
TAACCAGGTG ACTCAGGCGG TAGCGAAGCT CGGCATGTCC CAGATTCCAC AGAAGGACCT ATTGGAGACC GTTCATGTGA
 N  Q  V     T  Q  A     V  A  K  L     G  M  S     Q  I  P     Q  K  D  L     L  E  T     V  H  V>
       2010        2020        2030        2040        2050        2060        2070        2080
GAGAACAAGG GATGGTGAAG AAGCCCAAGC AGGAACTGCC TCCTCCGTTA ACAAAGGCTG AGCATGCTAT GCAAAAGAGA
 R  E  Q  G     M  V  K     K  P  K     Q  E  L  P     P  P  L     T  K  A     E  H  A  M     Q  K  R>
       2090        2100        2110        2120        2130        2140        2150        2160
TCAACCACCG AATTGGGAGA AAACCTGCAA GAATTAAGAG ACTTAACTCA AGAAATGGAA GTACATGCTG AAAAACTCAA
 S  T  T     E  L  G  E     N  L  Q     E  L  R     D  L  T  Q     E  M  E     V  H  A     E  K  L  K>
       2170        2180        2190        2200        2210        2220        2230        2240
ATGGCTGAAT AGAACTGAAT TGGAGATGCT TTCAGATAAA AGTCTGAGTT TACCTGAAAG GGATAAAATT TCAGAAAGCT
 W  L  N     R  T  E     L  E  M  L     S  D  K     S  L  S     L  P  E  R     D  K  I     S  E  S>
       2250        2260        2270        2280        2290        2300        2310        2320
TAAGGACTGT AAATATGACA TGGAATAAGA TTTGCAGAGA GGTGCCTACC ACCCTGAAGG AATGCATCCA GGAGCCCAGT
 L  R  T  V     N  M  T     W  N  K     I  C  R  E     V  P  T     T  L  K     E  C  I  Q     E  P  S>
       2330        2340        2350        2360        2370        2380        2390        2400
TCTGTTTCAC AGACAAGGAT TGCTGCTCAT CCTAATGTCC AAAAGGTGGT GCTAGTATCA TCTGCGTCAG ATATTCCTGT
 S  V  S     Q  T  R  I     A  A  H     P  N  V     Q  K  V  V     L  V  S     S  A  S     D  I  P  V>
       2410        2420        2430        2440        2450        2460        2470        2480
TCAGTCTCAT CGTACTTCGG AAATTTCAAT TCCTGCTGAT CTTGATAAAA CTATAACAGA ACTAGCCGAC TGGCTGGTAT
 Q  S  H     R  T  S     E  I  S  I     P  A  D     L  D  K     T  I  T  E     L  A  D     W  L  V>
       2490        2500        2510        2520        2530        2540        2550        2560
TAATCGACCA GATGCTGAAG TCCAACATTG TCACTGTTGG GGATGTAGAA GAGATCAATA AGACCGTTTC CCGAATGAAA
 L  I  D  Q     M  L  K     S  N  I     V  T  V  G     D  V  E     E  I  N     K  T  V  S     R  M  K>
       2570        2580        2590        2600        2610        2620        2630        2640
ATTACAAAGG CTGACTTAGA ACAGCGCCAT CCTCAGCTGG ATTATGTTTT TACATTGGCA CAGAATTTGA AAAATAAAGC
 I  T  K     A  D  L  E     Q  R  H     P  Q  L     D  Y  V  F     T  L  A     Q  N  L     K  N  K  A>
       2650        2660        2670        2680        2690        2700        2710        2720
TTCCAGTTCA GATATGAGAA CAGCAATTAC AGAAAAATTG GAAAGGGTCA AGAACCAGTG GGATGGCACC CAGCATGGCG
```

Figure 9 cont ...

```
          S  S  S     D  M  R     T  A  I  T     E  K  L     E  R  V     K  N  Q  W     D  G  T     Q  H  G>
         2730         2740         2750         2760         2770         2780         2790         2800
   TTGAGCTAAG   ACAGCAGCAG   CTTGAGGACA   TGATTATTGA   CAGTCTTCAG   TGGGATGACC   ATAGGGAGGA   GACTGAAGAA
    V  E  L  R     Q  Q  Q     L  E  D     M  I  I  D     S  L  Q     W  D  D     H  R  E  E     T  E  E>

2810         2820         2830         2840         2850         2860         2870         2880
   CTGATGAGAA   AATATGAGGC   TCGACTCTAT   ATTCTTCAGC   AAGCCCGACG   GGATCCACTC   ACCAAACAAA   TTTCTGATAA
    L  M  R     K  Y  E  A     R  L  Y     I  L  Q     Q  A  R  R     D  P  L     T  K  Q     I  S  D  N>

2890         2900         2910         2920         2930         2940         2950         2960
   CCAAATACTG   CTTCAAGAAC   TGGGTCCTGG   AGATGGTATC   GTCATGGCGT   TCGATAACGT   CCTGCAGAAA   CTCCTGGAGG
    Q  I  L     L  Q  E     L  G  P  G     D  G  I     V  M  A     F  D  N  V     L  Q  K     L  L  E>

2970         2980         2990         3000         3010         3020         3030         3040
   AATATGGGAG   TGATGACACA   AGGAATGTGA   AAGAAACCAC   AGAGTACTTA   AAAACATCAT   GGATCAATCT   CAAACAAAGT
    E  Y  G  S     D  D  T     R  N  V     K  E  T  T     E  Y  L     K  T  S     W  I  N  L     K  Q  S>

3050         3060         3070         3080         3090         3100         3110         3120
   ATTGCTGACA   GACAGAACGC   CTTGGAGGCT   GAGTGGAGGA   CGGTGCAGGC   CTCTCGCAGA   GATCTGGAAA   ACTTCCTGAA
    I  A  D     R  Q  N  A     L  E  A     E  W  R     T  V  Q  A     S  R  R     D  L  E     N  F  L  K>

3130         3140         3150         3160         3170         3180         3190         3200
   GTGGATCCAA   GAAGCAGAGA   CCACAGTGAA   TGTGCTTGTG   GATGCCTCTC   ATCGGGAGAA   TGCTCTTCAG   GATAGTATCT
    W  I  Q     E  A  E     T  T  V  N     V  L  V     D  A  S     H  R  E  N     A  L  Q     D  S  I>

3210         3220         3230         3240         3250         3260         3270         3280
   TGGCCAGGGA   ACTCAAACAG   CAGATGCAGG   ACATCCAGGC   AGAAATTGAT   GCCCACAATG   ACATATTTAA   AAGCATTGAC
    L  A  R  E     L  K  Q     Q  M  Q     D  I  Q  A     E  I  D     A  H  N     D  I  F  K     S  I  D>

3290         3300         3310         3320         3330         3340         3350         3360
   GGAAACAGGC   AGAAGATGGT   AAAAGCTTTG   GGAAATTCTG   AAGAGGCTAC   TATGCTTCAA   CATCGACTGG   ATGATATGAA
    G  N  R     Q  K  M  V     K  A  L     G  N  S     E  E  A  T     M  L  Q     H  R  L     D  D  M  N>

3370         3380         3390         3400         3410         3420         3430         3440
   CCAAAGATGG   AATGACTTAA   AAGCAAAATC   TGCTAGCATC   AGGGCCCATT   TGGAGGCCAG   CGCTGAGAAG   TGGAACAGGT
    Q  R  W     N  D  L     K  A  K  S     A  S  I     R  A  H     L  E  A  S     A  E  K     W  N  R>

3450         3460         3470         3480         3490         3500         3510         3520
   TGCTGATGTC   CTTAGAAGAA   CTGATCAAAT   GGCTGAATAT   GAAAGATGAA   GAGCTTAAGA   AACAAATGCC   TATTGGAGGA
    L  L  M  S     L  E  E     L  I  K     W  L  N  M     K  D  E     E  L  K     K  Q  M  P     I  G  G>

3530         3540         3550         3560         3570         3580         3590         3600
   GATGTTCCAG   CCTTACAGCT   CCAGTATGAC   CATTGTAAGG   CCCTGAGACG   GGAGTTAAAG   GAGAAAGAAT   ATTCTGTCCT
    D  V  P     A  L  Q  L     Q  Y  D     H  C  K     A  L  R  R     E  L  K     E  K  E     Y  S  V  L>

3610         3620         3630         3640         3650         3660         3670         3680
   GAATGCTGTC   GACCAGGCCC   GAGTTTTCTT   GGCTGATCAG   CCAATTGAGG   CCCCTGAAGA   GCCAAGAAGA   AACCTACAAT
    N  A  V     D  Q  A     R  V  F  L     A  D  Q     P  I  E     A  P  E  E     P  R  R     N  L  Q>

3690         3700         3710         3720         3730         3740         3750         3760
   CAAAAACAGA   ATTAACTCCT   GAGGAGAGAG   CCCAAAAGAT   TGCCAAAGCC   ATGCGCAAAC   AGTCTTCTGA   AGTCAAAGAA
    S  K  T  E     L  T  P     E  E  R     A  Q  K  I     A  K  A     M  R  K     Q  S  S  E     V  K  E>

3770         3780         3790         3800         3810         3820         3830         3840
   AAATGGGAAA   GTCTAAATGC   TGTAACTAGC   AATTGGCAAA   AGCAAGTGGA   CAAGGCATTG   GACAAACTCA   GAGACCTGCA
    K  W  E     S  L  N  A     V  T  S     N  W  Q     K  Q  V  D     K  A  L     E  K  L     R  D  L  Q>

3850         3860         3870         3880         3890         3900         3910         3920
   GGGAGCTATG   GATGACCTGG   ACGCTGACAT   GAAGGAGGCA   GAGTCCGTGC   GGAATGGCTG   GAAGCCCGTG   GGAGACTTAC
    G  A  M     D  D  L     D  A  D  M     K  E  A     E  S  V     R  N  G  W     K  P  V     G  D  L>

3930         3940         3950         3960         3970         3980         3990         4000
   TCATTGACTC   GCTGCAGGAT   CACATTGAAA   AAATCATGGC   ATTTAGAGAA   GAAATTGCAC   CAATCAACTT   TAAAGTTAAA
    L  I  D  S     L  Q  D     H  I  E     K  I  M  A     F  R  E     E  I  A     P  I  N  F     K  V  K>

4010         4020         4030         4040         4050         4060         4070         4080
   ACGGTGAATG   ATTTATCCAG   TCAGCTGTCT   CCACTTGACC   TGCATCCCTC   TCTAAAGATG   TCTCGCCAGC   TAGATGACCT
```

Figure 9 cont ...

```
         T  V  N     D  L  S  S     Q  L  S     P  L  D     L  H  P  S     L  K  M     S  R  Q     L  D  D  L>
         4090        4100       4110      4120      4130         4140        4150        4160
    TAATATGCGA  TGGAAACTTT  TACAGGTTTC  TGTGGATGAT  CGCCTTAAAC  AGCTTCAGGA  AGCCCACAGA  GATTTGGAC
     N  M  R     W  K  L     L  Q  V  S     V  D  D     R  L  K     Q  L  Q  E     A  H  R     D  F  G>
         4170        4180       4190      4200      4210         4220        4230        4240
    CATCCTCTCA  GCATTTTCTC  TCTACGTCAG  TCCAGCTGCC  GTGGCAAAGA  TCCATTTCAC  ATAATAAAGT  GCCCTATTAC
     P  S  S  Q     H  F  L     S  T  S     V  Q  L  P     W  Q  R     S  I  S     H  N  K  V     P  Y  Y>
         4250        4260       4270      4280      4290         4300        4310        4320
    ATCAACCATC  AAACACAGAC  CACCTGTTGG  GACCATCCTA  AAATGACCGA  ACTCTTTCAA  TCCCTTGCTG  ACCTGAATAA
     I  N  H     Q  T  Q  T     T  C  W     D  H  P     K  M  T  E     L  F  Q     S  L  A     D  L  N  N>
         4330        4340       4350      4360      4370         4380        4390        4400
    TGTACGTTTT  TCTGCCTACC  GTACAGCAAT  CAAAATCCGA  AGACTACAAA  AAGCACTATG  TTTGGATCTC  TTAGAGTTGA
     V  R  F     S  A  Y     R  T  A  I     K  I  R     R  L  Q     K  A  L  C     L  D  L     L  E  L>
         4410        4420       4430      4440      4450         4460        4470        4480
    GTACAACAAA  TGAAATTTTC  AAACAGCACA  AGTTGAACCA  AAATGACCAG  CTCCTCAGTG  TTCCAGATGT  CATCAACTGT
     S  T  T  N     E  I  F     K  Q  H     K  L  N  Q     N  D  Q     L  L  S     V  P  D  V     I  N  C>
         4490        4500       4510      4520      4530         4540        4550        4560
    CTGACAACAA  CTTATGATGG  ACTTGAGCAA  ATGCATAAGG  ACCTGGTCAA  CGTTCCACTC  TGTGTTGATA  TGTGTCTCAA
     L  T  T     T  Y  D  G     L  E  Q     M  H  K     D  L  V  N     V  P  L     C  V  D     M  C  L  N>
         4570        4580       4590      4600      4610         4620        4630        4640
    TTGGTTGCTC  AATGTCTATG  ACACGGGTCG  AACTGGAAAA  ATTAGAGTGC  AGAGTCTGAA  GATTGGATTA  ATGTCTCTCT
     W  L  L     N  V  Y     D  T  G  R     T  G  K     I  R  V     Q  S  L  K     I  G  L     M  S  L>
         4650        4660       4670      4680      4690         4700        4710        4720
    CCAAAGGTCT  CTTGGAAGAA  AAATACAGAT  ATCTCTTTAA  GGAAGTTGCG  GGGCCGACAG  AAATGTGTGA  CCAGAGGCAG
     S  K  G  L     L  E  E     K  Y  R     Y  L  F  K     E  V  A     G  P  T     E  M  C  D     Q  R  Q>
         4730        4740       4750      4760      4770         4780        4790        4800
    CTGGGCCTGT  TACTTCATGA  TGCCATCCAG  ATCCCCCGGC  AGCTAGGTGA  AGTAGCAGCT  TTTGGAGGCA  GTAATATTGA
     L  G  L     L  L  H  D     A  I  Q     I  P  R     Q  L  G  E     V  A  A     F  G  G     S  N  I  E>
         4810        4820       4830      4840      4850         4860        4870        4880
    GCCTAGTGTT  CGCAGCTGCT  TCCAACAGAA  TAACAATAAA  CCAGAAATAA  GTGTGAAAGA  GTTTATAGAT  TGGATGCATT
     P  S  V     R  S  C     F  Q  Q  N     N  N  K     P  E  I     S  V  K  E     F  I  D     W  M  H>
         4890        4900       4910      4920      4930         4940        4950        4960
    TGGAACCACA  GTCCATGGTT  TGGCTCCCAG  TTTTACATCG  AGTGGCAGCA  GCGGAGACTG  CAAAACATCA  GGCCAAATGC
     L  E  P  Q     S  M  V     W  L  P     V  L  H  R     V  A  A     A  E  T     A  K  H  Q     A  K  C>
         4970        4980       4990      5000      5010         5020        5030        5040
    AACATCTGTA  AAGAATGTCC  AATTGTCGGG  TTCAGGTATA  GAAGCCTTAA  GCATTTTAAC  TATGATGTCT  GCCAGAGTTG
     N  I  C     K  E  C  P     I  V  G     F  R  Y     R  S  L  K     H  F  N     Y  D  V     C  Q  S  C>
         5050        5060       5070      5080      5090         5100        5110        5120
    TTTCTTTTCG  GGTCGAACAG  CAAAAGGTCA  CAAATTACAT  TACCCAATGG  TGGAATATTG  TATACCTACA  ACATCTGGGG
     F  F  S     G  R  T     A  K  G  H     K  L  H     Y  P  M     V  E  Y  C     I  P  T     T  S  G>
         5130        5140       5150      5160      5170         5180        5190        5200
    AAGATGTACG  AGACTTCACA  AAGGTACTTA  AGAACAAGTT  CAGGTCGAAG  AAGTACTTTG  CCAAACACCC  TCGACTTGGT
     E  D  V  R     D  F  T     K  V  L     K  N  K  F     R  S  K     K  Y  F     A  K  H  P     R  L  G>
         5210        5220       5230      5240      5250         5260        5270        5280
    TACCTGCCTG  TCCAGACAGT  TCTTGAAGGT  GACAACTTAG  AGACTCCTAT  CACACTCATC  AGTATGTGGC  CAGAGCACTA
     Y  L  P     V  Q  T  V     L  E  G     D  N  L     E  T  P  I     T  L  I     S  M  W     P  E  H  Y>
         5290        5300       5310      5320      5330         5340        5350        5360
    TGACCCCTCA  CAATCTCCTC  AACTGTTTCA  TGATGACACC  CATTCAAGAA  TAGAACAATA  TGCCACACGA  CTGGCCCAGA
     D  P  S     Q  S  P     Q  L  F  H     D  D  T     H  S  R     I  E  Q  Y     A  T  R     L  A  Q>
         5370        5380       5390      5400      5410         5420        5430        5440
    TGGAAAGGAC  TAATGGGTCT  TTTCTCACTG  ATAGCAGCTC  CACCACAGGA  AGTGTGGAAG  ACGAGCACGC  CCTCATCCAG
```

Figure 9 cont ...

```
          M  E  R  T     N  G  S     F  L  T     D  S  S     T  T  G     S  V  E     D  E  H     A  L  I  Q>
         5450        5460        5470        5480        5490        5500        5510        5520
   CAGTATTGCC AAACACTCGG AGGAGAGTCC CCAGTGAGCC AGCCGCAGAG CCCAGCTCAG ATCCTGAAGT CAGTAGAGAG
     Q  Y  C     Q  T  L     G  G  E  S     P  V  S     Q  P  Q  S     P  A  Q     I  L  K     S  V  E  R>
         5530        5540        5550        5560        5570        5580        5590        5600
   GGAAGAACGT GGAGAACTGG AGAGGATCAT TGCTGACCTG GAGGAAGAAC AAAGAAATCT ACAGGTGGAG TATGAGCAGC
     E  E  R     G  E  L     E  R  I  I     A  D  L     E  E  E  Q     R  N  L     Q  V  E     Y  E  Q>
         5610        5620        5630        5640        5650        5660        5670        5680
   TGAAGGACCA GCACCTCCGA AGGGGGCTCC CTGTCGGTTC ACCGCCAGAG TCGATTATAT CTCCCCATCA CACGTCTGAG
     L  K  D  Q     H  L  R     R  G  L     P  V  G  S     P  P  E     S  I  I     S  P  H     T  S  E>
         5690        5700        5710        5720        5730        5740        5750        5760
   GATTCAGAAC TTATAGCAGA AGCAAAACTC CTCAGGCAGC ACAAGGTCG GCTGGAGGCT AGGATGCAGA TTTTAGAAGA
     D  S  E     L  I  A  E     A  K  L     L  R  Q     H  K  G  R     L  E  A     R  M  Q     I  L  E  D>
         5770        5780        5790        5800        5810        5820        5830        5840
   TCACAATAAA CAGCTGGAGT CTCAGCTCCA CCGCCTCCGA CAGCTGCTGG AGCAGCCTGA ATCTGATTCC CGAATCAATG
     H  N  K     Q  L  E     S  Q  L  H     R  L  R     Q  L  L     E  Q  P  E     S  D  S     R  I  N>
         5850        5860        5870        5880        5890        5900        5910        5920
   GTGTTTCCCC ATGGGCTTCT CCTCAGCATT CTGCACTGAG CTACTCGCTT GATCCAGATG CCTCCGGCCC ACAGTTCCAC
     G  V  S  P     W  A  S     P  Q  H     S  A  L  S     Y  S  L     D  P  D     A  S  G  P     Q  F  H>
         5930        5940        5950        5960        5970        5980        5990        6000
   CAGGCAGCGG GAGAGGACCT GCTGGCCCCA CCGCACGACA CCAGCACGGA TCTCACGGAG GTCATGGAGC AGATTCACAG
     Q  A  A     G  E  D  L     L  A  P     P  H  D     T  S  T  D     L  T  E     V  M  E     Q  I  H  S>
         6010        6020        6030        6040        6050
   CACGTTTCCA TCTTGCTGCC CAAATGTTCC CAGCAGGCCA CAGGCAATGT AATCACTAG
     T  F  P     S  C  C     P  N  V  P     S  R  P     Q  A  M     *>
```

Figure 9 cont ...

UTROPHIN GENE PROMOTER

The present invention is based on cloning of a genomic promoter region of the human utrophin gene and of the mouse utrophin gene.

The severe muscle wasting disorders Duchenne muscular dystrophy (DMD) and the less debilitating Becker muscular dystrophy (BMD) are due to mutations in the dystrophin gene resulting in a lack of dystrophin or abnormal expression of truncated forms of dystrophin, respectively. Dystrophin is a large cytoskeletal protein (427 kDa with a length of 125 nm) which in muscle is located at the cytoplasmic surface of the sarcolemma, the neuromuscular junction (NMJ) and myotendinous junction (MTJ). It binds to a complex of proteins and glycoproteins spanning the sarcolemma called the dystrophin associated glycoprotein complex (DGC). The breakdown of the integrity of this complex due to loss of, or impairment of dystrophin function, leads to muscle degeneration and the DMD phenotype.

The dystrophin gene is the largest gene so far identified in man, covering over 2.7 megabases and containing 79 exons. The corresponding 14 kb dystrophin mRNA is expressed predominantly in skeletal, cardiac and smooth muscle with lower levels in brain. Transcription of dystrophin in different tissues is regulated from either the brain promoter (predominantly active in neuronal cells) or muscle promoter (differentiated myogenic cells, and primary glial cells) giving rise to differing first exons. A third promoter between the muscle promoter and the second exon of dystrophin regulates expression in cerebellar Purkinje neurons. Recently reviewed in (Tinsley, et al (1994) *Proc Natl Acad Sci USA* 91, 8307–13, Blake, et al (1994) *Trends in Cell Biol.* 4: 19–23, Tinsley, et al (1993) *Curr Opin Genet Dev.* 3: 484–90).

There are various approaches which have been adopted for the gene therapy of DMD, using the mdx mouse as a model system. However, there are considerable problems related to the number of muscle cells that can be made dystrophin positive, the levels of expression of the gene and the duration of expression (Partridge, et al. (1995) *British Medical Bulletin* 51: 123–137). It has also become apparent that simply re-introducing genes expressing the dystrophin carboxy-terminus has no effect on the dystrophic phenotype although the DGC appears to be re-established at the sarcolemma (Cox, et al. (1994) *Nature Genet* 8: 333–339, Greenberg, et al. (1994) *Nature Genet* 8: 340–344).

In order to circumvent some of these problems, possibilities of compensating for dystrophin loss using a related protein, utrophin, are being explored as an alternative route to dystrophin gene therapy. A similar strategy is currently being evaluated in clinical trials to up-regulate foetal haemoglobin to compensate for the affected adult-globin chains in patients with sickle cell anaemia (Rodgers, et al. (1993) *N Engl J Med.* 328: 73–80, Perrine, et al. (1993) *N Engl J Med.* 328: 81–86).

Utrophin is a 395 kDa protein encoded by multiexonic 1 Mb UTRN gene located on chromosome 6q24 (Pearce, et al. (1993) *Hum Mol Gene.* 2: 1765–1772). At present the tissue regulation of utrophin is not fully understood. In the dystrophin deficient mdx mouse, utrophin levels in muscle remain elevated soon after birth compared with normal mice; once the utrophin levels have decreased to the adult levels (about 1 week after birth), the first signs of muscle fibre necrosis are detected. However there is evidence to suggest that in the small calibre muscles, continual increased levels of utrophin can interact with the DGC complex (or an antigenically related complex) at the sarcolemma thus preventing loss of the complex with the result that these muscles appear normal. There is also a substantial body of evidence demonstrating that utrophin is capable of localising to the sarcolemma in normal muscle. During fetal muscle development there is increased utrophin expression, localised to the sarcolemma, up until 18 weeks in the human and 20 days gestation in the mouse. After this time the utrophin sarcolemmal staining steadily decreases to the significantly lower adult levels shortly before birth where utrophin is localised almost exclusively to the NMJ. The decrease in utrophin expression coincides with increased expression of dystrophin. See reviews (Ibraghimov Beskrovnaya, et al. (1992) *Nature* 355, 696–702, Blake, et al. (1994) *Trends in Cell Biol*, 4: 19–23, Tinsley, et al. (1993) *Curr Opin Genet Dev.* 3: 484–90).

Thus, in certain circumstances utrophin can localise to the sarcolemma probably at the same binding sites as dystrophin, through interactions with actin and the DGC. Accordingly, if expression of utrophin is sufficiently elevated, it may maintain the DGC and thus alleviate muscle degeneration in DMD/BMD patients (Tinsley, et al. (1993) *Neuromuscul Disord* 3, 537–9).

However, manipulation of utrophin expression and screening for molecules able to upregulate expression is hampered by the limited understanding of utrophin expression regulation and its promoters. We have previously isolated a promoter element lying within the CpG island at the 5' end of the utrophin locus that is active in a broad range of cell types and tissues, and shown it to be synaptically regulated in vivo (Dennis, et al. (1996) *Nucleic Acids Res* 24, 1646–52 and WO 96/34101). The sequence contains a consensus N-box, a 6 bp motif important in the regulation of other genes expressed at the NMJ (Koike, et al. (1995) *Proc Natl Acad Sci USA* 92, 10624–10628). Localisation of utrophin at the NMJ in mature muscle is partially attributable to enhanced transcription of utrophin at sub-junctional myonuclei, with consequent synaptic accumulation of mRNA (Gramolini, et al. (1997) *J Biol Chem* 272, 8117–20, Vater, et al. (1998) *Molecular and Cellular Neuroscience* 10, 229–242). The utrophin promoter drives synaptic transcription of a reporter gene in vivo; this expression pattern is abolished by point mutations within the N-box (Gramolin, et al. (1998) J Biol Chem 273, 736–43).

The present inventors hypothesised that utrophin might be transcribed from more than one promoter, an important consideration for the following reasons: First, it may be undesirable to interfere with the mechanisms underlying synaptic regulation of genes, as this might affect expression of other post-synaptic components and impair the structure and function of the NMJ; a promoter without synaptic regulatory elements might be a more suitable target for pharmacological manipulation. Second, cardiac dysfunction is a common feature of the dystrophinopathies (Hoogerwaard, et al. (1997) *J Neurol* 244, 657–63, Sasaki, et al. (1998) *Am Heart J* 135, 937–44); if the cardiac utrophin message was transcribed from a different promoter, then it might prove necessary to up-regulate this. Finally, inclusion of additional regulatory sequences might increase the yield of a screening program to identify small molecules capable of transcriptional activation of utrophin.

We have now identified an alternative promoter lying within the large second intron of the utrophin gene, 50 kb 3' to exon 2. The promoter is highly regulated, expressed in a wide range of tissues and has little similarity to the synaptically expressed promoter. This promoter drives transcription of a widely expressed unique first exon that splices into a common full-length mRNA at exon 3. This unique exon (called exon IB) encodes a novel 31 amino acid N-terminus for the utrophin protein which may be involved in binding to the muscle membrane. The sequences of the two utrophin promoters are dissimilar, and we predict that they respond to discrete sets of cellular signals.

Exon IB is primarily considered herein to encode the indicated 31 amino acids. However, the splice occurs within a codon for aspartate. This aspartate residue is common to both isoforms of utrophin. In embodiments of the invention an aspartate residue may be included C-terminal to the 31 amino acids to provide a 32 amino acid peptide, which may be joined to additional amino acids, for instance additional utrophin sequence as discussed. See, for instance, FIG. 8 (SEQ ID NO:7) for one embodiment.

These findings significantly contribute to the understanding of the molecular physiology of utrophin expression and are important because the promoter reported here provides an alternative target for transcriptional activation of utrophin in DMD muscle. This promoter does not contain synaptic regulatory elements and might, therefore, be a more suitable target for pharmacological manipulation than the previously described promoter.

We have now cloned this alternative utrophin promoter and exon, and the present invention in various aspects and embodiments is based on the sequence information obtained and provided herein.

One major use of the promoter is in screening for substances able to modulate its activity. It is well known that pharmaceutical research leading to the identification of a new drug generally involves the screening of very large numbers of candidate substances, both before and even after a lead compound has been found. This is one factor which makes pharmaceutical research very expensive and time-consuming. A method or means assisting in the screening process will have considerable commercial importance and utility. Substances identified as upregulators of the utrophin promoter represent an advance in the fight against muscular dystrophy since they provide basis for design and investigation of therapeutics for in vivo use.

In one aspect, the present invention provides an isolated nucleic acid comprising a promoter, the promoter comprising a sequence of nucleotides shown in FIG. 1 (SEQ ID NO:1) or FIG. 2 (SEQ ID NO:3). The promoter may comprise one or more fragments of the sequence shown in FIG. 1 of FIG. 2 sufficient to promote gene expression. The promoter may comprise or consist essentially of a sequence of nucleotides 5' to position 1440 in FIG. 1 (human) or position 1183 in FIG. 2 (mouse). Preferably the promoter comprises or consists essentially of nucleotides 1199 to 1440 of the human sequence shown in FIG. 1, or the equivalent sequence in mouse, e.g. nucleotides 959 to 1183 of FIG. 2.

An even smaller portion of this part of the sequences shown in FIG. 1 of FIG. 2 may be used as long as promoter activity is retained. Restriction enzymes or nucleases may be used to digest the nucleic acid, followed by an appropriate assay (for example as illustrated herein using luciferase constructs) to determine the minimal sequence required. A preferred embodiment of the present invention provides a nucleic acid isolate with the minimal nucleotide sequence shown in FIG. 1 or FIG. 2 required for promoter activity. The minimal promoter element is situated between the PvuII restriction site at position 1199 in the human sequence and the transcription start site at 1440 bp in the human sequence and between nucleotides 959 to 1183 in the mouse sequence (see FIG. 2).

In one embodiment a promoter according to the present invention comprises or consists of sequence that is shown in FIG. 3 to be conserved between the human and mouse sequences, e.g. the 25 nucleotide sequence: ACAGGA-CATCCCAGTGTGCAGTTCG (SEQ ID NO:10) spanning the transcriptional start site.

The promoter may comprise one or more sequence motifs or elements conferring developmental and/or tissue-specific regulatory control of expression. For instance, the promoter may comprise a sequence for muscle-specific expression, e.g. an E-box element/myoD binding site, such as CANNTG, preferably CAGGTG.

Other regulatory sequences may be included, for instance as identified by mutation or digest assay in an appropriate expression system or by sequence comparison with available information, e.g. using a computer to search on-line databases.

By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

The present invention extends to a promoter which has a nucleotide sequence which is allele, mutant, variant or derivative, by way of nucleotide addition, insertion, substitution or deletion of a promoter sequence as provided herein. Systematic or random mutagenesis of nucleic acid to make an alteration to the nucleotide sequence may be performed using any technique known to those skilled in the art. One or more alterations to a promoter sequence according to the present invention may increase or decrease promoter activity, or increase or decrease the magnitude of the effect of a substance able to modulate the promoter activity.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction. Use of a reporter gene as discussed further below facilitates determination of promoter activity by reference to protein production.

In various embodiments of the present invention a promoter which has a sequence that is a fragment, mutant, allele, derivative or variant, by way of addition, insertion, deletion or substitution of one or more nucleotides, of the sequence of either the human or the mouse promoters shown in FIGS. 1 and 2, respectively, has at least about 60% homology with one or both of the shown sequences, preferably at least about 70% homology, more preferably at least about 80% homology, more preferably at least about 90% homology, more preferably at least about 95% homology. The sequence in accordance with an embodiment of the invention may hybridise with one or both of the shown sequences, or the complementary sequences (since DNA is generally double-stranded).

Similarity or homology (the terms are used interchangeably) or identity is preferably determined using GAP, from version 20 of GCG. This uses the algorithm of Needleman and Wunsch to align sequences inserting gaps as appropriate to improve the agreement between the two sequences. Parameters employed are the default ones: for nucleotide sequences—Gap Weight 50, Length Weight 3, Average Match 10.000, Average Mismatch 0.000; for peptide sequences—Gap Weight 8, Length Weight 2, Average Match 2.912, Average Mismatch−2.003. Peptide similarity scores are taken from the BLOSUM62 matrix. Also useful is the TBLASTN program, of Altschul et al. (1990) *J. Mol. Biol.* 215: 403–10, or BestFit, which is part of the Wisconsin Package, Version 8, September 1994, (Genetics Computer Group, 575 Science Drive, Madison, Wis., USA, Wisconsin 53711). Sequence comparisons may be made using FASTA and FASTP (see Pearson & Lipman, 1988. Methods in Enzymology 183: 63–98). Parameters are preferably set, using the default matrix, as follows: Gapopen (penalty for the first residue in a gap): −12 for proteins/−16 for DNA; Gapext (penalty for additional residues in a gap): −2 for proteins/−4 for DNA; KTUP word length: 2 for proteins/6 for DNA.

Nucleic acid sequence homology may be determined by means of selective hybridisation between molecules under stringent conditions.

Preliminary experiments may be performed by hybridising under low stringency conditions. For probing, preferred conditions are those which are stringent enough for there to be a simple pattern with a small number of hybridisations identified as positive which can be investigated further.

For example, hybridizations may be performed, according to the method of Sambrook et al. (below) using a hybridization solution comprising: 5×SSC (wherein 'SSC'=0.15 M sodium chloride; 0.15 M sodium citrate; pH 7), 5× Denhardt's reagent, 0.5–1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes. One common formula for calculating the stringency conditions required to achieve hybridization between nucleic acid molecules of a specified sequence homology is (Sambrook et al., 1989): $T_m=81.5°$ C.$+16.6$ Log [Na+]$+0.41$ (% G+C)$-0.63$ (% formamide)$-600/\#$bp in duplex.

As an illustration of the above formula, using [Na+]= [0.368] and 50−% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

It is well known in the art to increase stringency of hybridisation gradually until only a few positive clones remain. Other suitable conditions include, e.g. for detection of sequences that are about 80–90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

In a further embodiment, hybridisation of nucleic acid molecule to an allele or variant may be determined or identified indirectly, e.g. using a nucleic acid amplification reaction, particularly the polymerase chain reaction (PCR). PCR requires the use of two primers to specifically amplify target nucleic acid, so preferably two nucleic acid molecules with sequences characteristic of the utrophin promoter are employed. Using RACE PCR, only one such primer may be needed (see "PCR protocols; A Guide to Methods and Applications", Eds. Innis et al, *Academic Press*, New York, (1990)).

Thus a method involving use of PCR in obtaining nucleic acid according to the present invention may include:
  (a) providing a preparation of nucleic acid, e.g. from a muscle cell;
  (b) providing a pair of nucleic acid molecule primers useful in (i.e. suitable for) PCR, at least one of said primers being a primer specific for nucleic acid according to the present invention;
  (c) contacting nucleic acid in said preparation with said primers under conditions for performance of PCR;
  (d) performing PCR and determining the presence or absence of an amplified PCR product.

The presence of an amplified PCR product may indicate identification of an allele or other variant. The sequence may have the ability to promote transcription (i.e. have "promoter activity") in muscle cells, e.g. human muscle cells, or muscle-specific transcription.

Further provided by the present invention is a nucleic acid construct comprising a utrophin promoter region or a fragment, mutant, allele, derivative or variant thereof able to promoter transcription, operably linked to a heterologous gene, e.g. a coding sequence. By "heterologous" is meant a gene other than utrophin. Modified forms of utrophin are generally excluded. Generally, the gene may be transcribed into mRNA which may be translated into a peptide or polypeptide product which may be detected and preferably quantitated following expression. A gene whose encoded product may be assayed following expression is termed a "reporter gene", i.e. a gene which "reports" on promoter activity.

The reporter gene preferably encodes an enzyme which catalyses a reaction which produces a detectable signal, preferably a visually detectable signal, such as a coloured product. Many examples are known, including β-galactosidase and luciferase. β-galactosidase activity may be assayed by production of blue colour on substrate, the assay being by eye or by use of a spectrophotometer to measure absorbance. Fluorescence, for example that produced as a result of luciferase activity, may be quantitated using a spectrophotometer. Radioactive assays may be used, for instance using chloramphenicol acetyltransferase, which may also be used in non-radioactive assays. The presence and/or amount of gene product resulting from expression from the reporter gene may be determined using a molecule able to bind the product, such as an antibody or fragment thereof. The binding molecule may be labelled directly or indirectly using any standard technique.

Those skilled in the art are well aware of a multitude of possible reporter genes and assay techniques which may be used to determine gene activity. Any suitable reporter/assay may be used and it should be appreciated that no particular choice is essential to or a limitation of the present invention.

Expression of a reporter gene from the promoter may be in an in vitro expression system or may be intracellular (in vivo). Expression generally requires the presence, in addition to the promoter which initiates transcription, a translational initiation region and transcriptional and translational termination regions. One or more introns may be present in the gene, along with mRNA processing signals (e.g. splice sites).

Systems for cloning and expression of a polypeptide are discussed further below.

The present invention also provides a nucleic acid vector comprising a promoter as disclosed herein. Such a vector may comprise a suitably positioned restriction site or other means for insertion into the vector of a sequence heterologous to the promoter to be operably linked thereto.

Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Procedures for introducing DNA into cells depend on the host used, but are well known.

Thus, a further aspect of the present invention provides a host cell containing a nucleic acid construct comprising a promoter element, as disclosed herein, operably linked to a heterologous gene. A still further aspect provides a method comprising introducing such a construct into a host cell. The introduction may employ any available technique, including, for eukaryotic cells, calcium phosphate transfection, DEAE-Dextran transfection, electroporation, liposome-mediated transfection and transduction using retrovirus.

The introduction may be followed by causing or allowing expression of the heterologous gene under the control of the promoter, e.g. by culturing host cells under conditions for expression of the gene.

In one embodiment, the construct comprising promoter and gene is integrated into the genome (e.g. chromosome) of the host cell. Integration may be promoted by inclusion in the construct of sequences which promote recombination with the genome, in accordance with standard techniques.

Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1994, the disclosure of which is incorporated herein by reference.

Nucleic acid molecules, constructs and vectors according to the present invention may be provided isolated and/or purified (i.e. from their natural environment), in substantially pure or homogeneous form, free or substantially free of a utrophin coding sequence, or free or substantially free of nucleic acid or genes of the species of interest or origin other than the promoter sequence. Nucleic acid according to the present invention may be wholly or partially synthetic. The term "isolate" encompasses all these possibilities.

Nucleic acid constructs comprising a promoter (as disclosed herein) and a heterologous gene (reporter) may be employed in screening for a substance able to modulate utrophin promoter activity. For therapeutic purposes, e.g. for treatment of muscular dystrophy, a substance able to up-regulate expression of the promoter may be sought. A method of screening for ability of a substance to modulate activity of a utrophin promoter may comprise contacting an expression system, such as a host cell, containing a nucleic acid construct as herein disclosed with a test or candidate substance and determining expression of the heterologous gene. The level of transcription of the heterologous gene, or the level of heterologous protein may be determined. The level of protein may be determined by measuring the amount of protein, or the activity of the protein, using techniques known to those skilled in the art.

Alternatively, or additionally a method of screening for ability of a substance to modulate activity of a utrophin promoter may comprise contacting a cell containing an endogenous utrophin gene (e.g. a mammalian muscle cell) with a test substance and measuring the level of RNA transcription or protein expression using binding members specific for the nucleic acid or polypeptides disclosed herein. Specific binding members include antibodies and nucleic acid probes.

The level of expression in the presence of the test substance may be compared with the level of expression in the absence of the test substance. A difference in expression in the presence of the test substance indicates ability of the substance to modulate gene expression. An increase in expression of the heterologous gene compared with expression of another gene not linked to a promoter as disclosed herein indicates specificity of the substance for modulation of the utrophin promoter.

A promoter construct may be transfected into a cell line using any technique previously described to produce a stable cell line containing the reporter construct integrated into the genome. The cells may be grown and incubated with test compounds for varying times. The cells may be grown in 96 well plates to facilitate the analysis of large numbers of compounds. The cells may then be washed and the reporter gene expression analysed. For some reporters, such as luciferase, the cells will be lysed then analysed. Previous experiments testing the effects of glucocorticoids on the endogenous utrophin protein and RNA levels in myoblasts have already been described [12, 13] and techniques used for those experiments may similarly be employed.

Constructs comprising one or more developmental and/or time-specific regulatory motifs (as discussed) may be used to screen for a substance able to modulate the corresponding aspect of the promoter activity, e.g. muscle-specific expression.

Following identification of a substance which modulates or affects utrophin promoter activity, the substance may be investigated further. Furthermore, it may be manufactured and/or used in preparation, i.e. manufacture or formulation, of a composition such as a medicament, pharmaceutical composition or drug. These may be administered to individuals.

As noted above, the inventors also identified a novel coding sequence (Exon IB) which encodes a novel utrophin N-terminus.

According to a further aspect of the present invention there is provided a nucleic acid molecule which has a nucleotide sequence encoding a polypeptide which includes the amino acid sequence shown in FIG. 1 (SEQ ID NO:2) or FIG. 2 (SEQ ID NO:4). Such a polypeptide may include other utrophin sequences, and the nucleic acid molecule may be in the form of a utrophin "mini-gene" (discussed further below).

Such a polypeptide may include non-utrophin (i.e. heterologous or foreign) sequences and thereby form a larger fusion protein. For example, such a fusion protein could be used to target a non-utrophin polypeptide to muscle membranes.

The coding sequence included may be that shown in FIG. 1 or FIG. 2 or it may be a mutant, variant, derivative or allele of the sequence shown. The sequence may differ from that shown by a change which is one or more of addition, insertion, deletion and substitution of one or more nucleotides of the sequence shown. Changes to a nucleotide sequence may result in an amino acid change at the protein level, or not, as determined by the genetic code.

Thus, nucleic acid according to the present invention may include a sequence different from the sequences shown in FIG. 1 or FIG. 2 yet encode a polypeptide with the same amino acid sequence. The amino acid sequences shown in FIG. 1 and FIG. 2 consist of 31 residues.

On the other hand the encoded polypeptide may comprise an amino acid sequence which differs by one or more amino acid residues from the amino acid sequences shown in FIG. 1 or FIG. 2. Nucleic acid encoding a polypeptide which is an amino acid sequence mutant, variant, derivative or allele of the sequences shown in FIG. 1 and FIG. 2 are further provided by the present invention. Nucleic acid encoding such a polypeptide may show at the nucleotide sequence and/or encoded amino acid level greater than about 60% homology with the coding sequence and/or the amino acid sequence shown in FIG. 1 or FIG. 2, greater than about 70% homology, greater than about 80% homology, greater than about 90% homology or greater than about 95% homology. Determination of homology is discussed elsewhere herein.

A polypeptide which is a variant, allele, derivative or mutant may have an amino acid sequence which differs from that given in a figure herein by one or more of addition, substitution, deletion and insertion of one or more amino acids. Preferred such polypeptides have wild-type function, that is to say have one or more of the following properties: immunological cross-reactivity with an antibody reactive the polypeptide for which the sequence is given in FIG. 1 or FIG. 2; sharing an epitope with the polypeptide for which the amino acid sequence is shown in FIG. 1 or FIG. 2 (as determined for example by immunological cross-reactivity between the two polypeptides); a biological activity which is inhibited by an antibody raised against the polypeptide whose sequence is shown in FIG. 1 or FIG. 2; ability to bind muscle membrane, ability to bind actin; ability to bind DPC.

Variations in amino acid sequence include "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Particular amino acid sequence variants may differ from that shown in FIG. 1 or FIG. 2 by insertion, addition, substitution or deletion of 1 amino acid, 2, 3, 4, or 5–10 amino acids.

According to one aspect of the present invention there is provided a nucleic acid molecule comprising a sequence of nucleotides encoding a polypeptide with utrophin function. Utrophin nucleotide sequences which may be included in the nucleic acid molecule are disclosed in WO 97/922696 which is incorporated herein by reference.

See also FIG. 8 and FIG. 9 for disclosure of nucleic acid molecules and polypeptides according to the present invention, comprising the exon IB sequence of the invention.

A polypeptide with utrophin function is able to bind actin and able to bind the dystrophin protein complex (DPC).

The nucleic acid molecule may be an isolate, or in an isolated and/or purified form, that is to say not in an environment in which it is found in nature, removed from its natural environment. It may be free from other nucleic acid obtainable from the same species, e.g. encoding another polypeptide.

In one embodiment, nucleic acid molecule is a "mini-gene", i.e. the polypeptide encoded does not correspond to full-length utrophin but is rather shorter, a truncated version (Utrophin mini-genes are discussed in WO97/22696). For instance, part or all of the rod domain may be missing, such that the polypeptide comprises an actin-binding domain and a DPC-binding domain but is shorter than naturally occurring utrophin. In a full-length utrophin gene including what are identified herein as exons 1A and 1B, the actin-binding domain is encoded by nucleotides 1–739, while the DPC-binding domain (CRCT) is encoded by nucleotides 8499–10301 (where 1 represents the start of translation). See also FIG. 8 (SEQ ID NO:5). The respective domains in the polypeptide encoded by a mini-gene according to the invention may comprise amino acids corresponding to those encoded by these nucleotides in the full-length coding sequence. In one embodiment, a minigene according to the present invention comprises or consists of the amino acid sequence encoded by nucleotides 1–739 and 8499–10301 of the A isoform of utrophin in which exon 1B as identified herein is substituted for exons 1A and 2A. The sequence of such a minigene can be constructed by the ordinary skilled person using information disclosed herein, taking into account the content of WO97/22696 and Tinsley et al, *Nature* (1996) 384:349. The nucleic acid sequence and predicted amino acid sequence encoded by a 'mini-gene' according to the present invention are shown in FIG. 9 (SEQ ID NO:8).

Advantages of a mini-gene over a sequence encoding a full-length utrophin molecule or derivative thereof include easier manipulation and inclusion in vectors, such as adenoviral and retroviral vectors for delivery and expression.

A further preferred non-naturally occurring nucleic acid molecule encoding a polypeptide with the specified characteristics is a chimaeric construct wherein the encoding sequence comprises a sequence obtainable from one mammal, preferably human ("a human sequence"), and a sequence obtainable from another mammal, preferably mouse ("a mouse sequence"). Such a chimaeric construct may of course comprise the addition, insertion, substitution and/or deletion of one or more nucleotides with respect to the parent mammalian sequences from which it is derived. Preferably, the part of the coding sequence which encodes the actin-binding domain comprises a sequence of nucleotides obtainable from the mouse, or other non-human mammal, or a sequence of nucleotides derived from a sequence obtainable from the mouse, or other non-human mammal.

In a preferred embodiment, the sequence of nucleotides encoding the polypeptide comprises sequence GAGGCAC at residues 331–337 and/or the sequence GATTGTGGAT-GAAAACAGTGGG (SEQ ID NO:11) at residues 1453–1475 (using the conventional numbering from the initiation codon ATG), and a sequence obtainable from a human.

Nucleic acid according to the present invention is obtainable using one or more oligonucleotide probes or primers designed to hybridise with one or more fragments of a nucleic acid sequence shown in FIG. 1 or FIG. 2 particularly fragments of relatively rare sequence, based on codon usage or statistical analysis. The amino acid sequence information provided may be used in design of degenerate probes/primers or "long" probes. A primer designed to hybridise with a fragment of the nucleic acid sequence shown may be used in conjunction with one or more oligonucleotides designed to hybridise to a sequence in a cloning vector within which target nucleic acid has been cloned, or in so-called "RACE" (rapid amplification of cDNA ends) in which cDNA's in a library are ligated to an oligonucleotide linker and PCR is performed using a primer which hybridises with the sequence shown in the figures and a primer which hybridises to the oligonucleotide linker.

Nucleic acid isolated and/or purified from one or more cells (e.g. human, mouse) or a nucleic acid library derived from nucleic acid isolated and/or purified from cells (e.g. a cDNA library derived from mRNA isolated from the cells), may be probed under conditions for selective hybridisation and/or subjected to a specific nucleic acid amplification reaction such as the polymerase chain reaction (PCR).

A method may include hybridisation of one or more (e.g. two) probes or primers to target nucleic acid. Where the nucleic acid is double-stranded DNA, hybridisation will generally be preceded by denaturation to produce single-stranded DNA. The hybridisation may be as part of a PCR procedure, or as part of a probing procedure not involving PCR. An example procedure would be a combination of PCR and low stringency hybridisation. A screening procedure, chosen from the many available to those skilled in the art, is used to identify successful hybridisation events and isolated hybridised nucleic acid.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the DNA fragments on the filter and binding determined. DNA for probing may be prepared from RNA preparations from cells.

Preliminary experiments may be performed by hybridising under low stringency conditions various probes to Southern blots of DNA digested with restriction enzymes. Suitable conditions would be achieved when a large number of hybridising fragments were obtained while the background hybridisation was low. Using these conditions nucleic acid libraries, e.g. cDNA libraries representative of expressed sequences, may be searched.

It may be necessary for one or more gene fragments to be ligated to generate a full-length coding sequence. Also, where a full-length encoding nucleic acid molecule has not been obtained, a smaller molecule representing part of the full molecule, may be used to obtain full-length clones. Inserts may be prepared from partial cDNA clones and used to screen cDNA libraries.

Those skilled in the art are well able to employ suitable conditions of the desired stringency for selective hybridisation, taking into account factors such as oligonucleotide length and base composition, temperature and so on. Exemplary conditions have been discussed already above.

Nucleic acid according to the present invention may form part of a cloning vector and/or a vector from which the encoded polypeptide may be expressed. Polypeptide expression is discussed below. Suitable vectors can be chosen or constructed, containing appropriate and appropriately positioned regulatory sequences, as discussed elsewhere herein.

A further aspect of the present invention provides a polypeptide which comprises the amino acid sequence shown in FIG. 1 or FIG. 2. As mentioned earlier such a polypeptide may include other utrophin sequences or may include heterologous sequences.

Polypeptides which are amino acid sequence variants, alleles, derivatives or mutants are also provided by the present invention. Such polypeptides are discussed elsewhere herein.

The skilled person can use the techniques described herein and others well known in the art to produce large amounts of peptides, for instance by expression from encoding nucleic acid.

In a further aspect the invention provides a method of making a polypeptide, the method including expression from nucleic acid encoding the polypeptide (generally nucleic acid according to the invention). This may be conveniently be achieved by growing in culture a host cell containing such a vector, under suitable conditions which cause or allow expression of the polypeptide. Polypeptides may also be expressed in in vitro systems such as reticulocyte lysate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells and many others. A common, preferred bacterial host is *E. coli*.

Thus, a further aspect of the present invention provides a host cell containing heterologous nucleic acid encoding a polypeptide as disclosed herein.

The nucleic acid may be integrated into the genome (e.g. chromosome) of the host cell or may be on an extra-chromosomal vector within the cell, or otherwise identifiably heterologous or foreign to the cell.

A still further aspect provides a method comprising introducing such nucleic acid into a host cell. Suitable techniques are discussed elsewhere herein.

The introduction may be followed by causing or allowing expression from the nucleic acid, e.g. by culturing host cells under conditions for expression of the gene. The polypeptide encoded by the nucleic acid may be expressed from the nucleic acid in vitro, e.g. in a cell-free system or in cultured cells, or in vivo.

If the polypeptide is expressed coupled to an appropriate signal leader peptide it may be secreted from the cell into the culture medium.

Peptides can also be generated wholly or partly by chemical synthesis. The compounds of the present invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

The present invention also includes active portions, fragments, derivatives and functional mimetics of the polypeptides of the invention. An "active portion" of a polypeptide means a peptide which is less than said full length polypeptide, but which retains a biological activity, such as a biological activity selected from binding to ligand, binding to muscle membrane. Such an active fragment may be included as part of a fusion protein, e.g. including a polypeptide which is to be targetted to the muscle membrane.

A "fragment" of a polypeptide generally means a stretch of amino acid residues of about five to twenty-five contiguous amino acids, typically about ten to twenty contiguous amino acids. Fragments of the novel N-terminus polypeptide sequence may include antigenic determinants or epitopes useful for raising antibodies to a portion of the amino acid sequence, or may be sequence useful for targeting to muscle membrane. Alanine scans are commonly used to find and refine peptide motifs within polypeptides, this involving the systematic replacement of each residue in turn with the amino acid alanine, followed by an assessment of biological activity.

Preferred fragments of exon IB polypeptide include those comprising or consisting of an epitope which may be used for instance in raising or isolating antibodies. Variant and derivative peptides, peptides which have an amino acid sequence which differs from one of these sequences by way of addition, insertion, deletion or substitution of one or more amino acids are also provided by the present invention.

A "derivative" of a polypeptide or a fragment thereof may include a polypeptide modified by varying the amino acid sequence of the protein, e.g. by manipulation of the nucleic acid encoding the protein or by altering the protein itself. Such derivatives of the natural amino acid sequence may involve one or more of insertion, addition, deletion or substitution of one or more amino acids, which may be without fundamentally altering the qualitative nature of biological activity of the wild type polypeptide. Also encompassed within the scope of the present invention are functional mimetics of active fragments of the exon 1B polypeptides provided (including alleles, mutants, derivatives and variants). The term "functional mimetic" means a substance which may not contain an active portion of the relevant amino acid sequence, and probably is not a peptide at all, but which retains in qualitative terms biological activity of natural exon 1B polypeptide. The design and screening of candidate mimetics is described in detail below.

A polypeptide according to the present invention may be isolated and/or purified (e.g. using an antibody) for instance after production by expression from encoding nucleic acid (for which see below). Thus, a polypeptide may be provided free or substantially free from contaminants with which it is naturally associated (if it is a naturally-occurring polypeptide). A polypeptide may be provided free or substantially free of other polypeptides. Polypeptides according to the present invention may be generated wholly or partly by chemical synthesis. The isolated and/or purified polypeptide may be used in formulation of a composition, which may include at least one additional component, for example a pharmaceutical composition including a pharmaceutically acceptable excipient, vehicle or carrier. A composition including a polypeptide according to the invention may be used in prophylactic and/or therapeutic treatment as discussed below.

A polypeptide, peptide, allele, mutant, derivative or variant according to the present invention may be used as an immunogen or otherwise in obtaining specific antibodies. Antibodies are useful in purification and other manipulation of polypeptides and peptides, diagnostic screening and therapeutic contexts.

Accordingly, a further aspect of the present invention provides an antibody able to bind specifically to the polypeptide whose sequence is given in FIG. 1 or FIG. 2. Such an antibody may be specific in the sense of being able to distinguish between the polypeptide it is able to bind and other human (or mouse) polypeptides for which it has no or substantially no binding affinity (e.g. a binding affinity of about 1000× less). Specific antibodies bind an epitope on the molecule which is either not present or is not accessible on other molecules. Antibodies according to the present invention may be specific for the wild-type polypeptide. Antibodies according to the invention may be specific for a particular mutant, variant, allele or derivative polypeptide as between that molecule and the wild-type polypeptide, so as to be useful in diagnostic and prognostic methods as discussed below. Antibodies are also useful in purifying the polypeptide or polypeptides to which they bind, e.g. following production by recombinant expression from encoding nucleic acid.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80–82). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimicks that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge. Particular embodiments of antibodies according to the present invention include antibodies able to bind and/or which bind specifically, e.g. with an affinity of at least $10^7$ M, to the peptides shown in FIG. 1 (SEQ ID NO:2) or FIG. 2 (SEQ ID NO:4).

Antibodies according to the present invention may be used in screening for the presence of a polypeptide, for example in a test sample containing cells or cell lysate as discussed, and may be used in purifying and/or isolating a polypeptide according to the present invention, for instance following production of the polypeptide by expression from encoding nucleic acid therefor.

An antibody may be provided in a kit, which may include instructions for use of the antibody, e.g. in determining the presence of a particular substance in a test sample. One or more other reagents may be included, such as labelling molecules, buffer solutions, elutants and so on. Reagents may be provided within containers which protect them from the external environment, such as a sealed vial.

The present invention extends in various aspects not only to a substance identified using a nucleic acid molecule as a modulator of utrophin promoter activity, or to a polypeptide, or nucleic acid molecule in accordance with what is disclosed herein, but also a pharmaceutical composition, medicament, drug or other composition comprising such a substance, a method comprising administration of such a composition to a patient, e.g. for increasing utrophin expression for instance in treatment of muscular dystrophy, use of such a substance in manufacture of a composition for administration, e.g. for increasing utrophin expression for instance in treatment of muscular dystrophy, and a method of making a pharmaceutical composition comprising admixing such a substance with a pharmaceutically acceptable excipient, vehicle or carrier, and optionally other ingredients.

Administration will preferably be in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practitioners and other medical doctors.

A composition may be administered alone or in combination with other treatments, either simultaneously or sequentially dependent upon the condition to be treated.

Pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Instead of a substance identified using a promoter as disclosed herein, a mimetic or mimick or the substance may be designed for pharmaceutical use. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, eg peptides are unsuitable active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property.

Firstly, the particular parts of the compound that are critical and/or important in determining the target property are determined. In the case of a peptide, this can be done by systematically varying the amino acid residues in the peptide, eg by substituting each residue in turn. These parts or residues constituting the active region of the compound are known as its "pharmacophore".

Once the pharmacophore has been found, its structure is modelled to according its physical properties, eg stereochemistry, bonding, size and/or charge, using data from a range of sources, eg spectroscopic techniques, X-ray diffraction data and NMR. Computational analysis, similarity mapping (which models the charge and/or volume of a pharmacophore, rather than the bonding between atoms) and other techniques can be used in this modelling process. In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

Mimetics of substances identified as having ability to modulate utrophin promoter activity using a screening method as disclosed herein are included within the scope of the present invention.

Modifications to and further aspects and embodiments of the present invention will be apparent to those skilled in the art. All documents mentioned herein are incorporated by reference.

Experimental basis for and embodiments of the present invention will now be described in more detail, by way of example and not limitation, and with reference to the following figures:

BRIEF DESCRIPTION OF THE DRAWINGS

FIG. 1 shows the sequence of the human exon 1B and promoter B. Numbering corresponds to the insert of pBSX2.0. The deduced translation of exon 1B is shown. The positions of features such as restriction sites, IL-6 response element and Alu repetitive elements are shown.

Figure 2:
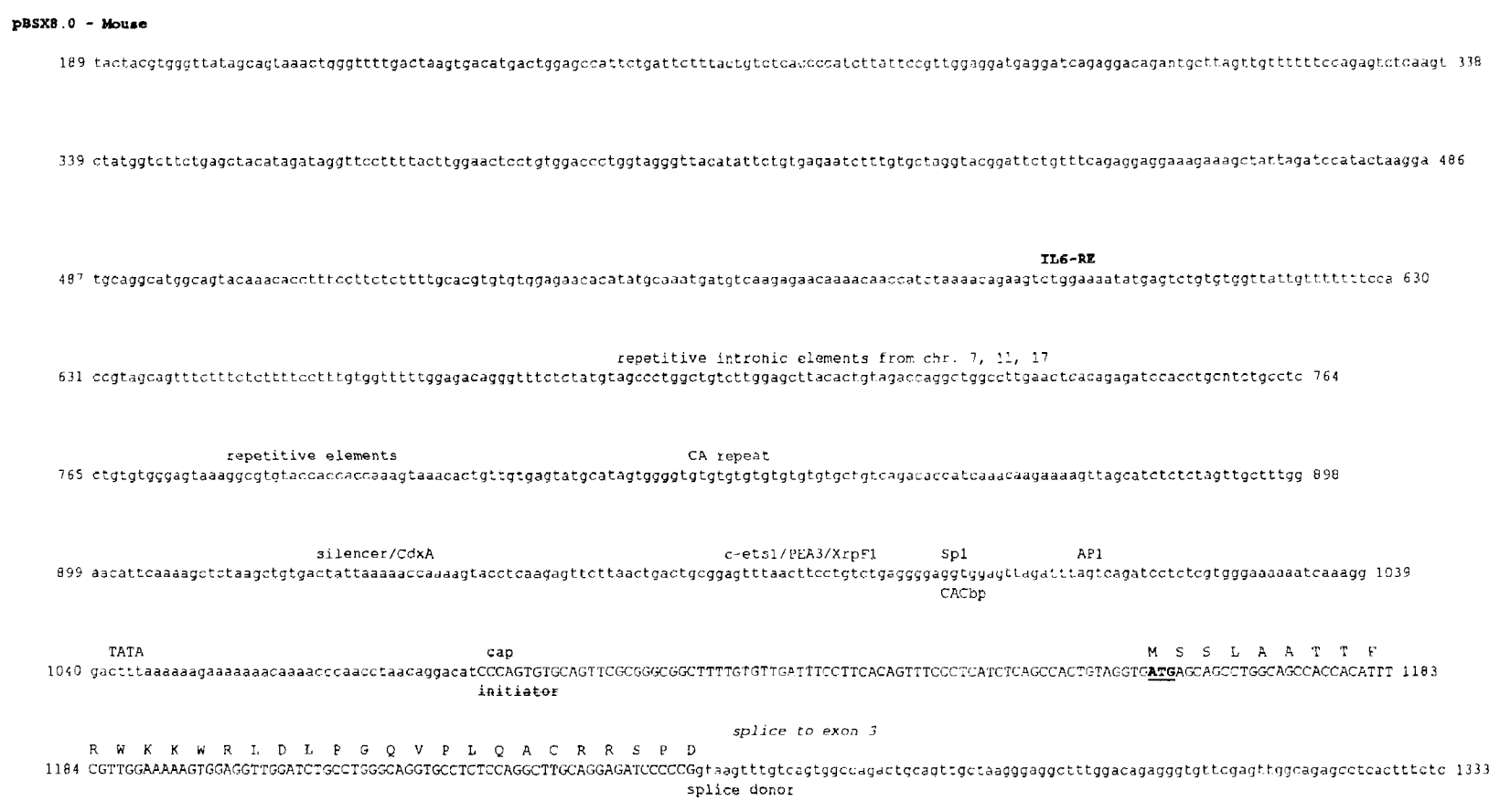

FIG. 2 shows the sequence of the mouse exon 1B and promoter B. Numbering corresponds to the insert of pBSX8.0. The deduced translation of exon 1B is shown. The positions of features such as restriction sites, IL-6 response element and Alu repetitive elements are shown.

FIG. 3 shows the sequence alignment of human (top) and mouse (bottom) exon 1B (in upper case) and promoter B. Numbering corresponds to the inserts of pBSX2.0 and pBSX8.0, respectively. The human PvuII site (see FIG. 7) is indicated. The open triangle indicates the position at which the luciferase coding sequence was inserted to make PGL3/ UtroB/F (see below). The deduced translation of exon 1B is shown; amino acids marked in bold type are identical between the human and mouse sequences. The conserved splice donor consensus is shown in grey. Two putative Ap1 sites and an initiator-like element (Inr) are 100% conserved and indicated in black. A solid arrow marks the single transcription start indicated by primer extension; figures adjacent to the sequence indicate the number of individual 5'RACE clones that terminated at the positions shown.

FIG. 5 shows a schematic representation of (A) human YAC and (B) mouse PAC contigs showing position of exons within the genomic map. Key to mouse restriction sites: C, ClaI; S, SacII; B, BssHII; X, XhoI. (C) shows the nomenclature for utrophin promoters, exons and transcripts.

FIG. 8 shows conceptual translation of exon 1B as part of utrophin, showing a nucleotide sequence and encoded polypeptide according to embodiments of the present invention.

FIG. 9 shows the nucleic acid and predicted amino acid sequence of a utrophin B isoform 'minigene'.

OLIGONUCLEOTIDES, PCR, RT-PCR AND 5'RACE

Figure 4:
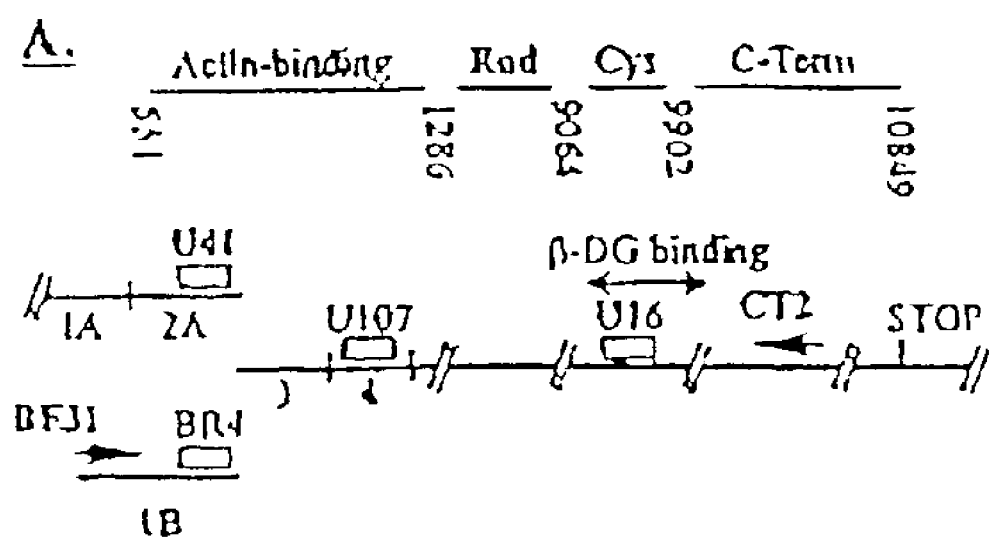
FIG. 4 shows the position of the primers used in RT-PCR of exon 1B-containing utrophin transcript, and the probes used to probe the PCR products. Primers specific to exon 1B (BF31) and utrophin C-terminus (CT2) were used to amplify 9816 bp of utrophin cDNA. The products were blotted and probed with U41, U107, BR4 and U16 as indicated. The diagram is not to scale; numbering refers to the nucleotide sequence of the full-length cDNA. The corresponding functional domains of the protein are indicated above: actin binding domain; rod, rod domain; Cys, cysteine rich domain, C-Term; C-terminal domain.

PCR and RT-PCR were performed as described (Blake, et al. (1996) *J Biol Chem* 271, 7802–7810). Oligonucleotide sequences (5' to 3') were:

| | | |
|---|---|---|
| UM83 | gatgttcctg tgaggccttc gag, | (SEQ ID NO:12) |
| UM82 | cactcttgga aaatcgagcg t, | (SEQ ID NO:13) |
| U16 | actatgatgt ctgccagagt tg, | (SEQ ID NO:14) |
| U107 | gatccaatag cttccttcca tcttt, | (SEQ ID NO:15) |
| UBF | tggaaaaagt ggaggttgga, | (SEQ ID NO:16) |
| BR2 | tccaacctcc actttttcca, | (SEQ ID NO:17) |
| BR4 | gcctggagag ctacatgccc t, | (SEQ ID NO:18) |
| BF8 | ctccacatct ttttcctcat catch, | (SEQ ID NO:19) |
| BF9 | gattgtggtg atggttgtag aa, | (SEQ ID NO:20) |
| BR10 | gattgtggtg atggttgtag aa, | (SEQ ID NO:20) |
| BR14 | gatgatgagg aaaagatgt ggag, | (SEQ ID NO:21) |

-continued

| BF15 | aaacccaaaa taacacagga catc, | (SEQ ID NO:22) |
| BF16 | agtgtaactt ctctctggtg, | (SEQ ID NO:23) |
| BF31 | taagcagatg taggtgatga gc, | (SEQ ID NO:24) |
| BF42 | gctgcttttg ttgtccactt c, | (SEQ ID NO:25) |
| BR43 | atagcttcct tccatctttg ag, | (SEQ ID NO:26) |
| CT2 | ctccacgttc ttccctctct act, | (SEQ ID NO:27) |
| 2ApF | gcgtgcagtg gaccattttt cagattta, | (SEQ ID NO:28) |
| 1BpF | cgctgcagca gccaccacat ttcgttg, | (SEQ ID NO:29) |
| 3pR | gcgtgcagat cgagcgttta tccatttg. | (SEQ ID NO:30) |

5' RACE was undertaken using adapter-ligated mouse heart cDNA (Marathon-Ready, Clontech), following the manufacturer's protocol, using the supplied adapter primers with nested mouse utrophin primers UM83 (exon 4) and UM82 (exon 3). Products were cloned in PGEM-T (Promega). Human exon 1B was isolated from skeletal muscle cDNA by PCR using mouse primers UBF and UM83. 5'RACE was used to clone the 5' end of human exon 1B, using primers U107 and BR4. Full-length utrophin RT-PCR was done as described (Blake, et al. (1996) *J Biol Chem* 271, 7802–7810), but using Boehringer Expand Reverse Transcriptase and Long Template PCR reagents, and a primer annealing temperature of 59° C. Semi-quantitative RT-PCR was performed using primers BF42 and BR43 to amplify utrophin B, and commercial primers (Stratagene) to amplify glyceraldehyde-3-phosphate dehydrogenase (GAPDH). Exponential amplification was established by withdrawing samples from thermal cycling at 1 cycle intervals over a range of 5 cycles, predicted to span the exponential range following initial experiments in which samples were withdrawn at 5 cycle intervals. Products were blotted and probed with labelled BR4 or a 600 bp GA3PH probe. Band intensities were quantified using a Storm phosphoimager. A graph of $\log_2$ [band intensity] versus cycle number showed a linear relationship with gradient=1, indicating near-perfect exponential amplification. The band intensities at any given cycle over this range are therefore directly proportional to the amount of cDNA in the original samples.

Genomic Mapping and Clones

Human YACs are as previously described (Pearce, et al. (1993) *Hum Mol Genet* 2, 1765–72). Southern blots of restriction digested YAC DNA were probed with end-labelled BR4. A 3.0 kb hybridising XbaI fragment was cloned from YAC 4X124H10 (a YAC clone which contains a human genomic DNA insert) into pBlueScript (Stratagene) generating pBSX2.0. Mouse PACs were identified from the RPCI21 library. A 398 bp exon 1B/promoter B DNA probe (UB400) encompassing human positions 1129 to 1527 was used for exon 1B mapping. Library filters were screened with probes to exons 1A–5 (Dennis, et al. (1996) *Nucleic Acid Res* 24, 1646–52) and UB400. Eleven PACs were identified, and four of these arranged into a contig by restriction mapping. An 8.0 kb XbaI fragment from PAC 110C24, that hybridised with UB400, was cloned in pBlueScript generating pBSX8.0.

Northern Blots and Probes

A human multiple tissue northern blot and b-actin control cDNA probe were obtained from Clontech. A utrophin C-terminal cDNA probe, encompassing the last 4.0 kb of the utrophin message, was generated by PCR. Human exon 1B sequence between positions 1480 and 1596 was cloned into PGEM-T and an exon 1B antisense riboprobe was transcribed (In Vitro Transcription Kit, Promega) from the SP6 promoter following linearisation of the plasmid with NcoI. Hybridisation was carried out at 70° C. in 50% formamide hybridisation buffer (Ausubel, et al. (1999) *Current Protocols in Molecular Biology* (Wiley)) and the filter was washed at 75° C. in 0.1×SSC, 0.1% SDS for 2 hours.

RNase Protection

Specific probes spanning the exon 1B/3 and exon 2A/3 boundaries were obtained by PCR amplification of mouse heart cDNA using primers 2ApF, 1BpF and 3pR. Products were cloned in the PstI site of pDP18 (Ambion) and sequenced. Plasmids were linearised with EcoR1 (1B) or BamH1 (2A); labelled antisense riboprobe was transcribed from the T7 promoter and gel purified. RNase protection was carried out using RPAIII kit (Ambion) following the manufacturer's instructions (30 μg total RNA unless stated, hybridisation temperature 42° C., RNase A/T1 dilution 1:200). Following electrophoretic separation, band intensities were quantified as above, and corrected for the amount of label present in each protected fragment.

Promoter/Reporter Constructs

Reporter constructs were generated by PCR amplification of the human sequence between positions 39 and 1503, using pBSX2.0 as template. Pfu polymerase was used with primers BF9 and BR14. Following 15 cycles of 96° C. for 45 seconds, 62° C. for 45 seconds, 72° C. for 4 minutes, products were dA-tailed and cloned in pGEM-T. Clones were identified with product in both orientations and insert, liberated by digestion with SacI/NcoI, was cloned into the SacI/NcoI sites of a promoterless luciferase reporter plasmid (pGL3 basic, Promega), generating constructs with insert in forward (pGL3/utroB/F) and reverse (pGL3/UtroB/R) orientation with respect to the coding sequence of luciferase. Deletions of the forward construct were generated by cleavage at SpeI, NdeI, EcoRI and PvuII sites in the insert, followed by religation to sites in the 5' or 3' polylinker. Constructs were sequenced completely.

Cell Culture and Transfections

Three human cell lines (IN157 rhabdomyosarcoma (Nielsen et al., 1993, *Mol Cell Endocrinol* 93: 87–95), CL11T47 kidney epithelial and HeLa cervical epithelial (Cancer Research, 1952 12: 264) were maintained as described (Dennis, et al. (1996) *Nucleic Acid Res* 24, 1646–52). 2 μg pGL3/utroB/F or R, or its molar equivalent, mixed with 0.5 μg of LacZ control plasmid (pSV-β-gal, Promega) was transfected in each well of 6 well plates using Superfect (Qiagen), following the manufacturer's protocol. 48 hours later, cells were harvested and cell extracts were assayed for luciferase and β-galactosidase activity as described (Dennis, et al. (1996) *Nucleic Acids Res* 24, 1646–52). Luciferase activity was standardised to β-galactosidase activity in each individual sample to control for transfection efficiency. Results are expressed as mean luciferase/β-galactosidase ratio for four individual transfections. Error bars indicate the standard error of the mean. For comparison of different constructs within the same cell line, results were standardised to those obtained with pGL3/utroB/F and are expressed as % of this value. For comparison of constructs between cell lines, results were standardised to those obtained with a luciferase-SV40 promoter/enhancer plasmid (pGL3 control, Promega) that generates high levels of reporter activity in all cell lines tested.

Primer Extension

Primer extension was carried out as described (18); end-labelled primer BR2 was annealed to 0, 30 or 50 μg mouse heart total RNA at 58° C. for 20 minutes, and extended at 42° C. for 40 minutes. Products were separated on a 6% polyacrylamide gel, under denaturing conditions, alongside a sequencing ladder generated from pBSX8.0 using primer BR2.

Results

An alternative 5' Exon in Utrophin mRNA

Utrophin from a mouse heart cDNA library was amplified by 5'RACE, and the resulting products cloned and sequenced. Of 12 clones, 8 contained novel sequence 5' of exon 3. Below, we present evidence that the novel sequence is a single alternative 5' exon of utrophin containing a translational initiation codon. We refer to this sequence as 'exon 1B' to distinguish it from the previously described 5' cDNA sequence comprising untranslated exon 1A and exon 2A which contains the translational start (FIG. 5c).

Figure 3:
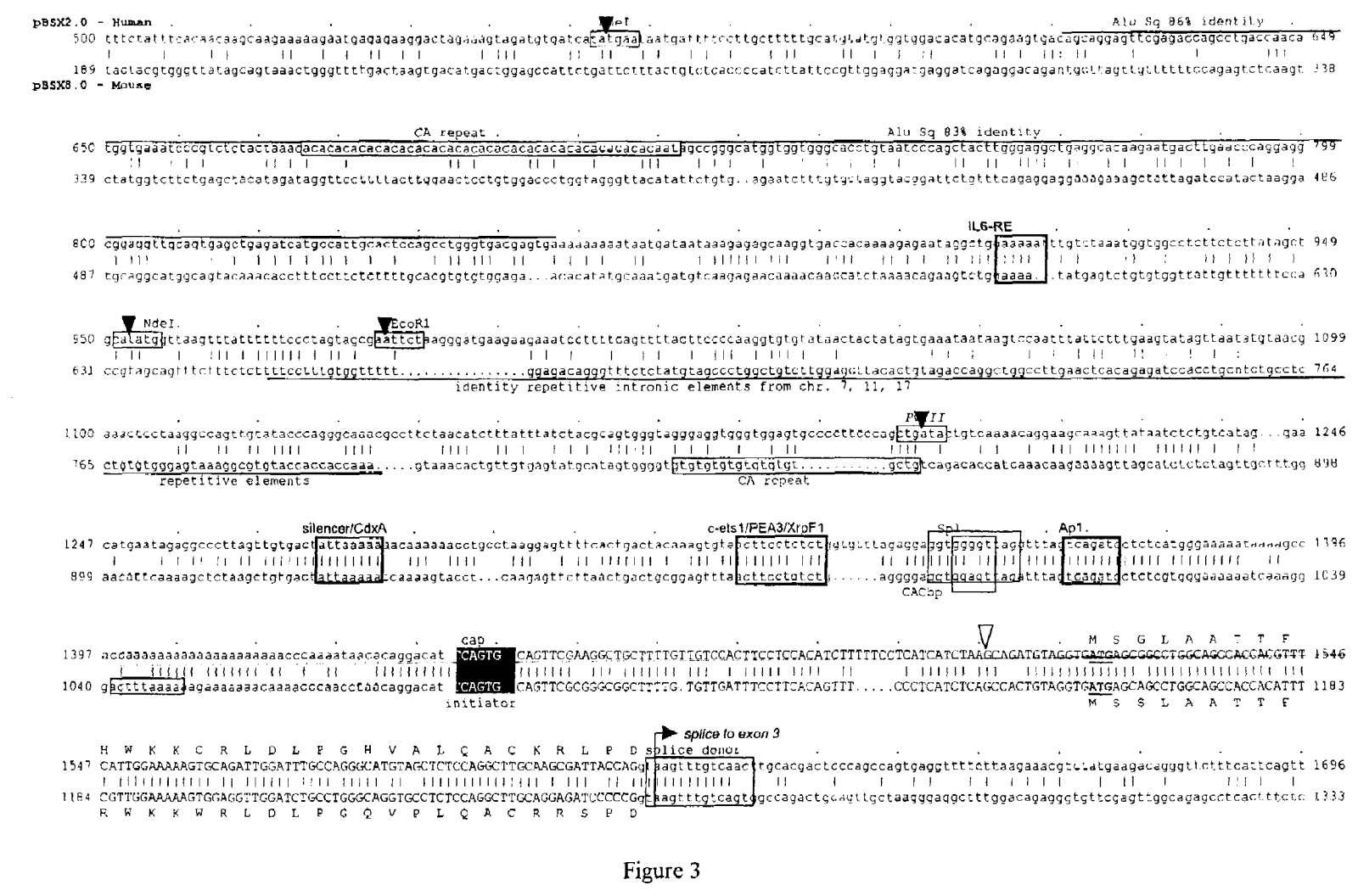

FIG. 3 shows a sequence comparison of human and mouse exon 1B, and genomic flanking sequence. The position and phase of the splice junction at the 5' end of exon 3 is identical for both exon 1- and exon 2A-containing transcripts. Exon 1B contains a putative ATG translation initiation codon and open reading frame, in-frame with that of exon 3, predicting a novel 31 amino acid N-terminus to the utrophin protein. The context of the ATG codon is predicted to be favourable for translation in that there is a purine at position −3 (bold in FIG. 3) (33). Human and mouse exons 1B show 82% nucleotide identity. The predicted translations are 84% identical and 94% similar. The position and context of the ATG codon are conserved. The human sequence contains a second putative ATG codon immediately 5' (position 1511, solid bar in FIG. 1), followed by a TAG stop codon. As this ATG does not adhere to the Kozak consensus, is not associated with an open reading frame and is not present in the mouse sequence, we predict that this is not a functional translation start. A similar feature is present in human exon 2A, where the 5'UTR contains a short open reading frame prior to the true translation start.

The Transcript Associated with Exon 1B

A human multiple tissue northern blot was probed with an exon 1B anti-sense riboprobe. A single hybridising 13 kb band was observed, identical to that produced by probing the same blot with a cDNA encompassing 4 kb of the utrophin C-terminus, indicating that exon 1B is exclusively associated with a full-length utrophin mRNA. Exon 1B is ubiquitously expressed, and appears most abundant in heart and pancreas, and least abundant in the brain, relative to β-actin. This is similar to the expression profile of total full-length utrophin.

RT-PCR was employed to confirm the association of exon 1B with a utrophin mRNA predicted to give rise to functional protein (FIG. 4). Amplification of first strand cDNA from IN157 cells utilising a forward primer specific to exon 1B (BF3I) and a reverse primer within the utrophin C-terminus (CT2) produced a product of expected size. Successive hybridisation of this PCR product with domain-specific probes; U41, UBR4, U107 and U16, confirmed that exon 1B is associated with a utrophin transcript spanning the full coding sequence of the gene.

The expression profiles of exons 1B and 2A were examined using RNase protection. Specific riboprobes corresponding to the exon 1B/3 and 2A/3 boundaries were simultaneously hybridised with total RNA, allowing direct quantitation of transcript abundance. B-utrophin is the most abundant form in the heart, whereas exon 2A-containing transcripts predominate in the kidney. Approximately equal amounts of exons 1B and 2A were observed in the brain and in skeletal muscle.

Mapping and Cloning of Genomic Sequence Associated with Exon 1B

Using probe BR4, exon 1B was mapped within our previously described human YAC contig (26) encompassing the 5' end of the utrophin locus (FIG. 5a). A hybridising band was seen with YAC 4X124H10 but not 4X23E3 or 5C2 indicating that exon 1B lies within the 120 kb intron 2 of the utrophin gene. A subsequent database search identified a clone from the HGMP human chromosome 6 sequencing project, containing exons 1A, 2A and 1B. This indicated that exon 1B lies 52.2 kb 3' of exon 2A (FIG. 5a). Probing the mouse genomic PAC library (RPCI21 from P. DeJong, Roswell Park Cancer Institute) with utrophin exons 1A, 1B and 2–5 inclusive identified a series of genomic PACs spanning the 5' end of the mouse utrophin gene. Four of these PACs were assembled into a contig of the region. Hybridisation with UB400 confirmed that exon 1B lies within intron 2 in the mouse (FIG. 5b), approximately 50 kb 3' of exon 2.

Human and mouse genomic fragments were obtained from the YAC and PAC libraries, respectively. Genomic sequence encompassing exon 1B was obtained by an Xba I digest of YAC 4X124H10 (human 3 kb fragment) and PAC110c24 (mouse 8.8 kb fragment). These fragments were sub-cloned into pBluescript vector, the human fragment was deleted to 2 kb during the sub-cloning. The plasmid clones were designated pBSX2.0 (human) and pBSX8.0 (mouse). Comparison of the cDNA and genomic sequence showed no evidence of a further 5' exon in the transcript associated with exon 1B, suggesting that the genomic flanking sequence contained the transcription start and promoter element responsible for exon 1B expression. Our nomenclature for utrophin 5' exons, transcripts and promoters appears in FIG. 5c.

Figure 6:
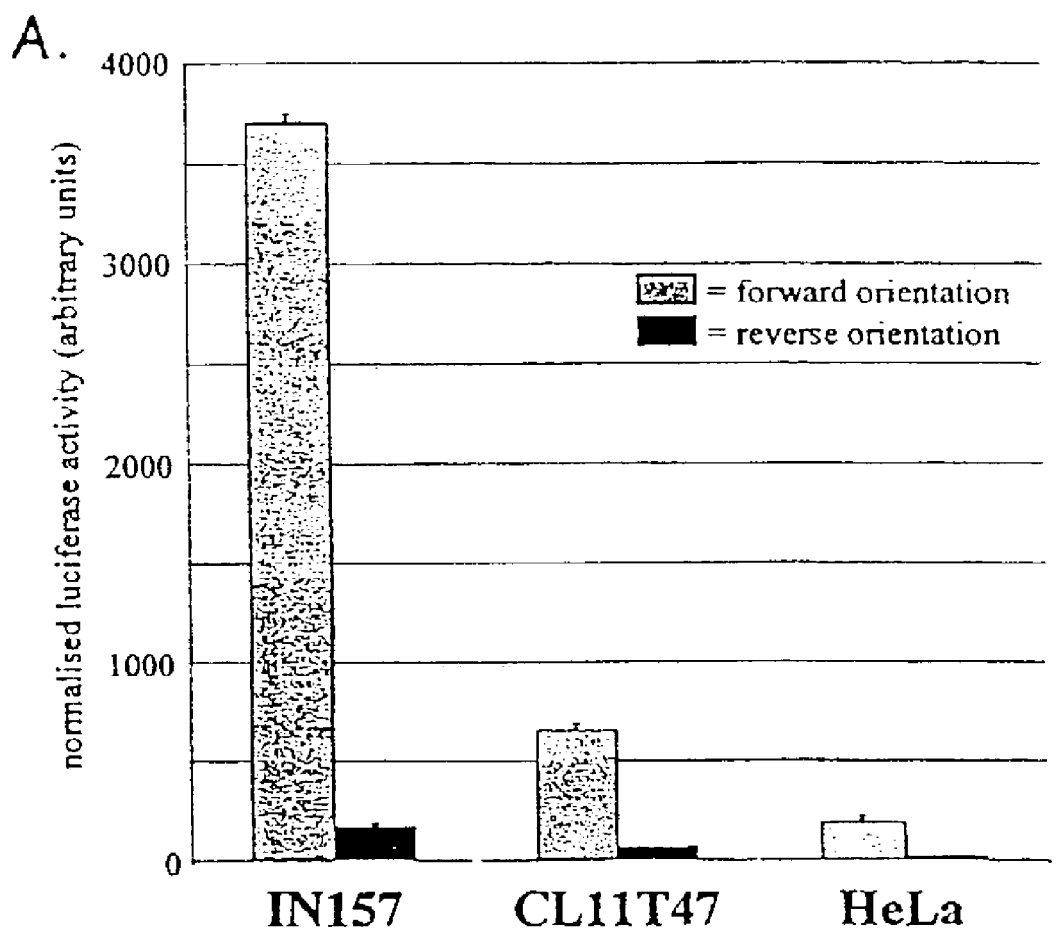
FIG. 6 shows the in vitro activity of utrophin promoter B. (A) shows normalised luciferase activity following transfection of three different human cell types with either pGL3/ utroB/F ('forward construct') or pGL3/utroB/R ('reverse construct').

Promoter B 1.5 kb of human genomic sequence 5' of exon 1B, including the 5'UTR of exon 1B, was cloned in both orientations into a promoterless luciferase reporter vector. Three human cell lines (IN157 rhabdomyosarcoma, CL11T47 kidney epithelial and HeLa cervical epithelial) were transiently transfected with these constructs. These three lines were chosen because they are known to express utrophin mRNA and protein at different levels. Reporter activity was detected at significantly higher levels in cells transfected with the forward than the reverse orientation construct, indicating promoter activity (FIG. 6). Interestingly, the level of activity varied between cell lines by an order of magnitude. Semi-quantitative RT-PCR demonstrated that the variation of luciferase expression mimicked the transcription profile of endogenous utrophin exon 1B. In contrast, the GA3PDH control showed identical amplification in all cDNA samples, indicating that the differences seen in B-utrophin amplification have arisen from differences in the level of expression of the endogenous B-utrophin transcript in these cells lines. These data show that the 1.5 kb of genomic sequence 5' of exon 1B utilised in these reporter clones contains the necessary signals to initiate transcription of exon 1B, and regulatory elements that determine the level of expression in these cell lines.

Figure 7:
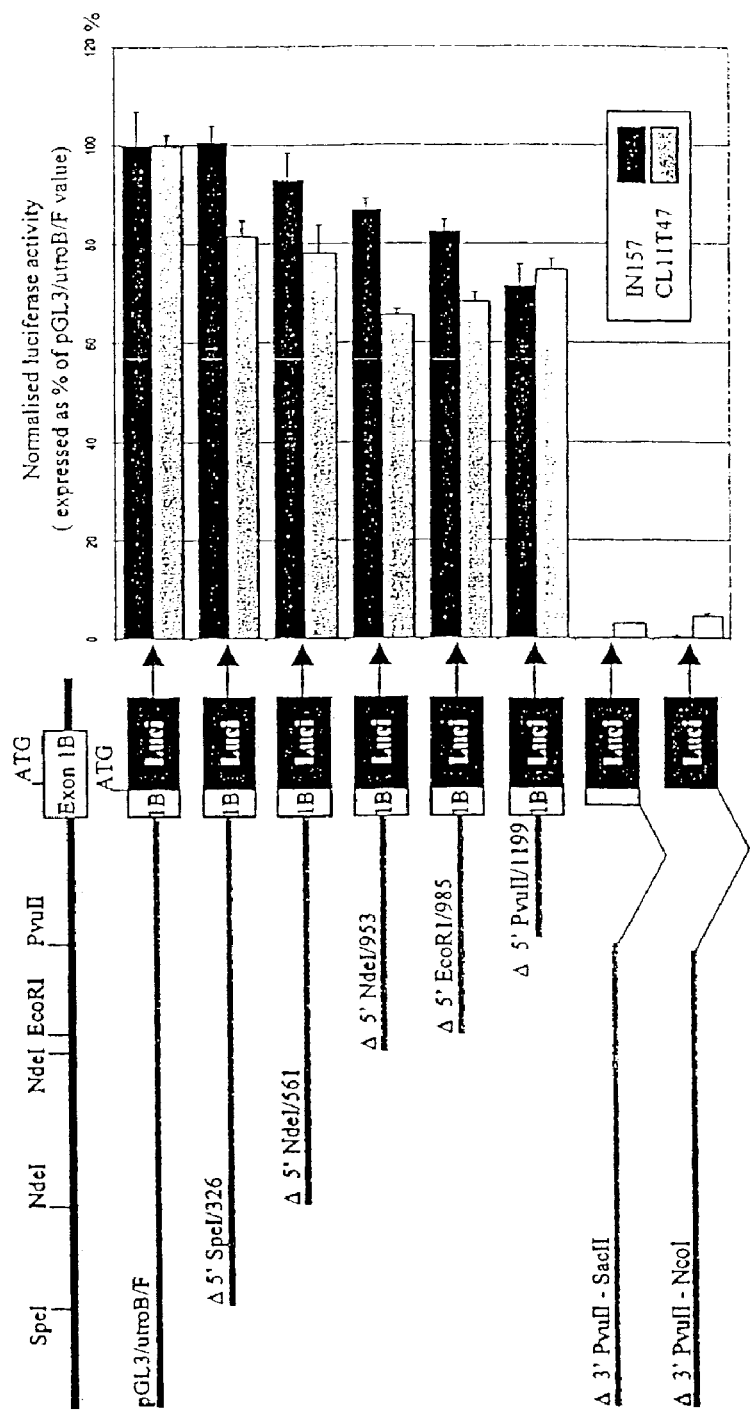
FIG. 7 shows deletion analysis of promoter B. The 1.5 kb insert of pGL3/utroB/F was deleted at its 5' and 3' ends using the internal restriction sites indicated. Reporter activity was assayed following transient transfection of IN157 and CL11T47 cells.

To further delineate important elements within this region, a series of 5' and 3' deletions of promoter B were made, and the in vitro activity of each one assayed (FIG. 7). A 300 bp element, contained within clone pGL3/utroB/F/D5' Pvu 1199, retains 70% activity of the full 1.5 kb construct in expressing cell lines, and shows 74% identity between human and mouse (FIG. 3). Homology falls to 50% when sequence further 5' if the human PvuII site is compared with corresponding mouse sequence using a 35 bp window. Homology was determined using GAP, from version 20 of GCG, with default parameters as noted already above.

Promoter B Transcription Start Site

The 5' ends of 8 human and 4 mouse 5'RACE clones clustered around a putative cap site in the genomic sequence (FIG. 3). None of the 5'RACE clones generated by amplification across the exon 3/exon 1B boundary extended further upstream. RT-PCR was carried out using forward primers around this region with a reverse primer in exon 4. A product of expected size was amplified from IN157 cDNA by primers BF42 and BF8, but not BF16 or BF15, indicating that the transcription start is within the 18 bp that separates the two primers BF15 and BF42. These 18 bases contain the putative cap site and the cluster of RACE clone 5' ends.

To map the start site accurately, primer extension using an exon 1B reverse primer and mouse heart RNA was employed. This yielded a single product, indicative of a single transcription start site. Transcription initiates at mouse position 1183 within a 25-bp motif, which is 100% conserved between human and mouse. Part of this motif, spanning the cap site, is a 6/7 base match for the initiator consensus, and correspondingly shows homology to the initiators of other genes. The transcription start site is homologous to the initiators of other promoters. Consensus 1, initiator consensus derived from sequence comparison of Inr⁺ genes (Azizkhan, et al. (1993) *Critical Reviews in Eukaryotic Gene Expression* 3, 229–254); consensus 2, experimentally-derived consensus for functional initiator (Javahery, et al. (1994) *Molecular and Cellular Biology* 14, 116–127); TdT, terminal deoxynucleotidyl transferase; hRAR, human retinoic acid receptor a; mCREB, mouse cAMP response element binding protein. Transcribed sequence is indicated in bold uppercase. We consider this promoter to be of the $TATA^-Inr^+$ type.

Assaying for Substances which Modulate Utrophin Promoter Activity

Method 1:

This method uses a mouse mdx-H2K myoblast line stably transfected with a human 7.0 kb utrophin promoter-luciferase construct. On day 1 myoblast cells transfected with the construct are plated out in 6-well dishes, with compound or DMSO-only for the negative controls.

4×6 well plates are used for every 3 compounds (the compounds are dissolved in DMSO and stored prior to use). For example, compound A, or B, or C were each added to 1 well, while the remaining 3 wells contain only DMSO. This results in 4 wells containing each compound and 12 wells with DMSO alone. Due to the inherent noise of both the harvesting/assay and cell seeding/growth steps, this is the minimum number that results in meaningful analysis. Setting up the plates in this way means that the data really are paired, and can be analysed with a paired student T test. This provides a more powerful statistical analysis rather than putting each compound on a different plate and comparing it with a control plate.

On Day 4 the cells are harvested and luciferase quantitation and pairwise analysis is carried out.

Method 2:

Compounds which up-regulate the endogenous utrophin promoter are be found using mdx-H2K myoblasts that are not transfected with the utrophin promoter-luciferase construct. Mdx-myoblasts can be used to mimic utrophin transcription and protein stability in dystrophin-deficient cells.

Identification of Utrophin Protein Expression

Quantitative Western Blotting is used to measure the level of utrophin expression (Tinsley J M, et al., *Nature Medicine* 4, 1441–1444.) Using 6 well plates and treating with compound as described above generates enough total protein sample to test by Western blotting. Antibodies specific to the A protein or B protein are used to quantify levels of either protein.

Identification of Utrophin RNA Expression

Quantitative ribonuclease protection is used to analyse levels of utrophin expression. A pairwise design is used, as described above, but more cells are necessary. To see bands clearly, about 20–30 μg total RNA is used. Each compound and control will need a 175 cm² tissue culture flask. A dual probe to simultaneously identify the A transcript and B transcript is be used.

Using the two techniques described compounds are identified after cell treatment which modulate utrophin levels. The same techniques are used for in vivo animal experiments where the compound is administered to dystrophin deficient mdx mice.

Interleukin-6 (IL-6) Interactions

Two related elements are present in the promoters of genes encoding acute phase proteins that mediate an increase in transcription stimulated by an IL-6 triggered signalling cascade (Hocke et al., 1992). One of these was found to be present in the exon 1B flanking sequence. Wild type and mutated reporter fusions for IL-6 were therefore tested for responsiveness in appropriate cell systems.

Constructs of the 1.5F B promoter normal and mutant (consensus change: ctggaa>gatatca concerning the mutant: Hattori M et al (1990) *Proc. Natl. Acad. Sci. USA*. March; 87(6):2364–8) were introduced into a promoter-less luciferase reporter vector and transfected into IN157 cells with a *renilla* firefly control. Cells were washed and charcoal stripped serum added 5 hours post-transfection and left overnight. IL-6 amounts were added as illustrated with an appropriate amount of IL-6 soluble receptor. The cells were left for 24 hours and then assayed for activity using a luminometer.

Figure 10:
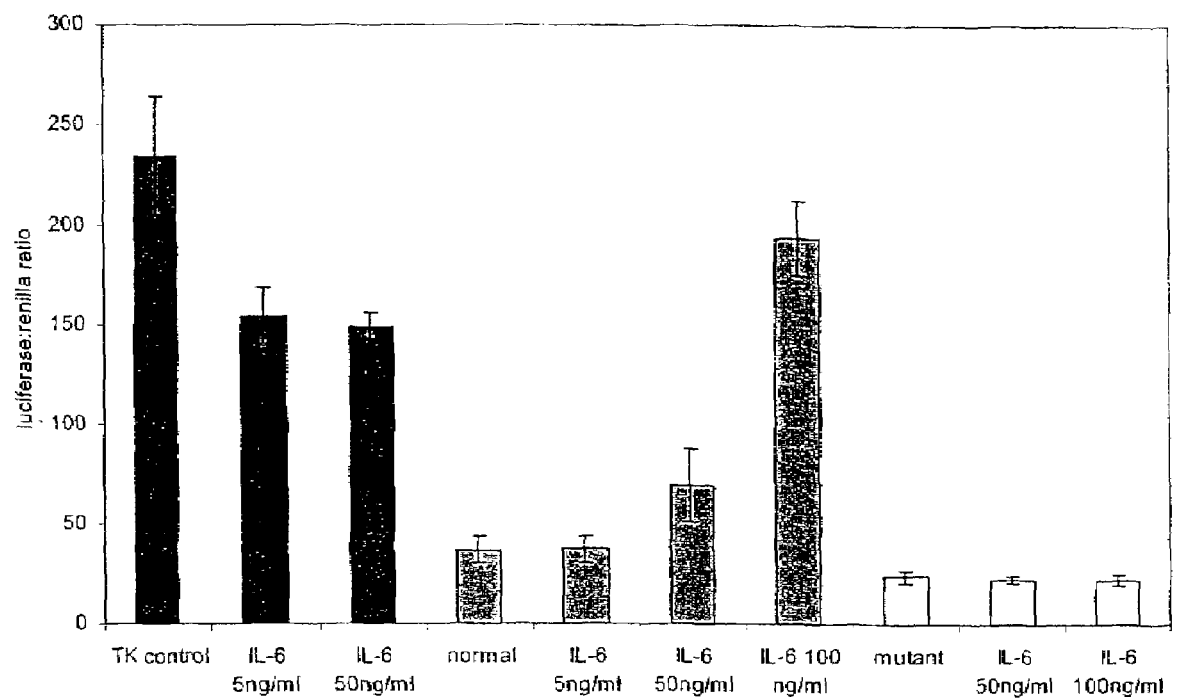
FIG. 10 shows the dosage dependence of IL-6 mediated expression from the isoform B promoter.

A dosage dependent transcriptional response was noted in the normal, but not the mutated reporter construct (FIG. 10). This result indicates the existence of a cytokine mediated signalling pathway which causes up-regulation of the B utrophin promoter through the interaction of IL-6 and IL-6 receptor with the conserved IL-6 response element.

Discussion

We have demonstrated that there is a second promoter within intron 2 of the utrophin gene, driving expression of a unique first exon that splices into a common 13 kb mRNA. These data are important, both in terms of understanding the molecular physiology of utrophin expression, and in view of their application to therapeutic intervention in DMD.

The functional consequences of genes having more than one promoter have been postulated (reviewed in (Ayoubi, et al (1996) *FASEB J.* 10,453–460). A single gene may achieve a complex temporal and spatial expression pattern by interaction of different promoters with discrete subsets of transcription factors. Dystrophin is an example: three dissimilar promoters are active at different levels in specific cell types within the heart, skeletal muscle and the brain (Gorecki, et al. (1992) *Hum Mol Genet* 1, 505–510, Barnea, et al. (1990) *Neuron* 5, 881–888, Holder, et al. *Human Genetics* 97, 232–239). Northern blot analysis, however, indicates that utrophin exon 1B is ubiquitously expressed, implying that promoters A and B are co-expressed in many tissues. It is conceivable that examination of transcript distribution in whole tissue samples has masked cell type-specific patterns of expression. Data from isolated human cell lines in vitro support this notion; we observed large differences in promoter B activity between different cell lines, consistent with an in vivo expression profile involving specific cellular populations. Alternatively, the two promoters may be spatially regulated at a sub-cellular level. Within adult skeletal muscle fibres, promoter A is synaptically driven (Gramolini, et al. (1997) *J Biol Chem* 272, 8117–20), yet aggregates of utrophin mRNA are detectable at up to 25% extrasynaptic nuclei (Vater, et al. (1998) *Molecular and cellular Neuroscience* 10, 229–242). Expression of promoter B in the extrasynaptic compartment might be invoked as one possible explanation.

A second proposed function of alternative promoters is the generation of transcripts with interchangeable 5' exons, giving rise to mRNAs with alternative 5'UTRs or proteins with novel N-terminal domains. Unlike exon 1B, utrophin exon 1A contains a long GC-rich 5'UTR. In some transcripts, GC-rich 5'UTRs are not translated efficiently (Kozak, M. (1991) *J Cell Biol* 115, 887–903), and there are examples of genes in which alternative use of GC-rich and non-GC-rich 5'UTRs has been implicated in post-transcriptional regulation of protein synthesis (Nielson, et al. (1990) *J Biol Chem* 265, 13431–13434). In addition, the predicted 31 amino acids encoded by exon 1B are different to the 26 amino acids of exon 2A; the functions of the resulting N-termini may be different.

The discovery of a second promoter provides a new target for the upregulation of utrophin to ameliorate the DMD phenotype. Promoter B is highly regulated, probably by different factors from promoter A, including IL-6. Elucidation of the mechanisms responsible for the large difference in promoter B activity between IN157 and HeLa cells might lead to identification of a factor that can be delivered to muscle to activate utrophin expression. Importantly, as the N-box motif is absent from promoter B, this is unlikely to carry any risk of NMJ disruption potentially inherent in the pharmacological manipulation of synaptically regulated promoter A.

The invention claimed is:

1. An isolated nucleic acid comprising a promoter which comprises a sequence of nucleotides comprising the sequence ACAGGACATCCCAGTGTGCAGTTCG (SEQ. ID. NO. 10) free of utrophin coding sequence.

2. An isolated nucleic acid according to claim 1 consisting essentially of a promoter which comprises the sequence of nucleotides shown 5' to position 1440 in FIG. 1.

3. An isolated nucleic acid according to claim 1 consisting essentially of a promoter which comprises the nucleotides numbered 1199–1440 in the sequence shown in FIG. 1.

4. An isolated nucleic acid consisting of a promoter which comprises a sequence having at least 90% identity with the sequence of nucleotides shown 5' to position 1440 in FIG. 1 or having at least 90% identity with the nucleotides numbered 1199–1440 in FIG. 1 and which promoter, when operably linked to a sequence of nucleotides, has the ability to initiate transcription of that sequence, said transcription being muscle-specific.

5. A nucleic acid construct comprising a promoter the sequence ACAGGACATCCCAGTGTGCAGTTCG (SEQ. ID. NO. 10) operably linked to a heterologous sequence.

6. A nucleic acid construct according to claim 5 wherein the heterologous sequence is a coding sequence.

7. A nucleic acid construct according to claim 6 wherein said coding sequence encodes a reporter molecule.

8. An in vitro host cell comprising a nucleic acid construct according to claim 6.

9. An in vitro host cell comprising a nucleic acid construct according to claim 7.

10. A method comprising culturing a host cell according to claim 8 under conditions for expression of the peptide or polypeptide encoded by said coding sequence.

11. A method as claimed in claim 10 wherein said coding sequence encodes a reporter molecule.

12. A method according to claim 10 comprising detection of transcription of said coding sequence.

13. A method according to claim 10 comprising detection of expression of the peptide or polypeptide encoded by said coding sequence.

14. An isolated nucleic acid molecule comprising a nucleotide sequence encoding a polypeptide including the amino acid sequence shown in FIG. 1 (SEQ. ID. NO.2).

15. An isolated nucleic acid molecule comprising a nucleotide sequence encoding a polypeptide that is an allele, mutant or derivative of a polypeptide including the amino acid sequence shown in FIG. 1, which amino acid sequence has at least 90% identity with the polypeptide sequence in FIG. 1.

16. An isolated nucleic acid molecule comprising a nucleotide sequence encoding a polypeptide having the amino acid sequence shown in FIG. 9 (SEQ. ID. NO.9).

17. An isolated nucleic acid molecule comprising the nucleotide sequence shown in FIG. 9 (SEQ. ID. NO.8).

18. A nucleic acid of any one of claims 14, 15, 16 and 17 comprised in a vector.

19. A nucleic acid according to any one of claims 14, 15, 16 and 17 comprised in an expression vector.

20. An in vitro host cell containing an expression vector according to claim 19.

21. A method including introduction of nucleic acid according to any of claims 14, 15, 16 and 17 into a cell.

22. A method as claimed in claim 21 wherein said nucleic acid is an expression vector.

23. A method according to claim 21 wherein said introduction takes place in vitro.

24. A method as claimed in claim 21 which includes causing or allowing expression of said polypeptide encoding nucleotide sequence in a cell.

25. A method according to claim 24 wherein the cell is part of a mammal.

26. A method according to claim 24 wherein the expression product is purified and/or isolated following expression.

27. A method according to claim 26 wherein the expression product is formulated into a composition which includes at least one additional component, following purification and/or isolation of the expression product.

28. A nucleic acid construct comprising a promoter which comprises the nucleotides numbered 1199–1440 in the sequence shown in FIG. 1, operably linked to a heterologous sequence.

29. A nucleic acid construct comprising a promoter which comprises the sequence of nucleotides shown 5' to position 1440 in FIG. 1, operably linked to a heterologous sequence.

30. A nucleic acid construct comprising a promoter which comprises a sequence having at least 90% identity with the sequence of nucleotide shown 5' to position 1440 in FIG. 1 or having at least 90% identity with the nucleotides numbered 1199–1440 in FIG. 1, operably linked to a heterologous sequence.

31. A nucleic acid construct according to claim 28 wherein the heterologous sequence is a coding sequence.

32. A nucleic acid construct according to claim 29 wherein the heterologous sequence is a coding sequence.

33. A nucleic acid construct according to claim 30 wherein the heterologous sequence is a coding sequence.

* * * * *

SEQUENCE LISTING

```
<160> NUMBER OF SEQ ID NOS: 30

<210> SEQ ID NO 1
<211> LENGTH: 1197
<212> TYPE: DNA
<213> ORGANISM: Homo sapiens

<400> SEQUENCE: 1
tttctatttc acaacaagca agaaaaagaa tgagagaagg actagaaagt agatgtgatc      60
atatgaataa tgattttcct tgcttttttgc atgtatgtgg tggacacatg cagaagtgac    120
agcaggagtt cgagaccagc ctgaccaaca tggtgaaatc ccgtctctac taaacacaca    180
cacacacaca cacacacaca cacacacaca cacacacaca atagccgggc atggtggtgg    240
gcacctgtaa tcccagctac ttgggaggct gaggcacaag aatgacttga acccaggagg    300
cggaggttgc agtgagctga gatcatgcca ttgcactcca gcctgggtga cgagtgaaaa    360
aaaaataatg ataataaaga gagcaaggtg accacaaaag agaataggct ggaaaaattt    420
gtctaaatgg tggcctcttc tcttatagct gcatatggtt aagtttattt tttccctagt    480
agcgaattct aagggatgaa gaagaaatcc ttttcagttt tacttcccca aggtgtgtat    540
aactactata gtgaaataat aagtccaatt tattctttga agtatagtta atatgtaacg    600
aaactcctaa ggccagttgt atacccaggg caaacgcctt ctaacatctt tatttatcta    660
cgcagtgggt agggaggtgg gtggagtgcc ccttcccagc tgatactgtc aaaacaggaa    720
gcaaagttat aatctctgtc ataggaacat gaatagaggc ccttagttgt gactattaaa    780
aaaacaaaaa acctgcctaa ggagtttttca ctgactacaa agtgtaactt cctctctggt    840
gtttagagga ggtggggtta ggtttagtca gatcctctca tgggaaaaat aaaagccacc    900
aaaaaaaaaa aaaaaaaaaa cccaaaataa cacaggacat cccagtgtgc agttcgaagg    960
ctgcttttgt tgtccacttc ctccacatct tttcctcat catctaagca gatgtaggtg   1020
atgagcggcc tggcagccac cacgtttcat tggaaaaagt gcagattgga tttgccaggg  1080
```

```
catgtagctc tccaggcttg caagcgatta ccaggtaagt ttgtcaactt gcacgactcc    1140
cagccagtga ggttttctta agaaacgtct atgaagacag ggttctttca ttcagtt      1197
```

<210> SEQ ID NO 2
<211> LENGTH: 32
<212> TYPE: PRT
<213> ORGANISM: Homo sapiens

<400> SEQUENCE: 2

Met Ser Gly Leu Ala Ala Thr Thr Phe His Trp Lys Lys Cys Arg Leu
 1               5                  10                  15

Asp Leu Pro Gly His Val Ala Leu Gln Ala Cys Lys Arg Leu Pro Asp
                20                  25                  30

<210> SEQ ID NO 3
<211> LENGTH: 1145
<212> TYPE: DNA
<213> ORGANISM: Mus sp.
<220> FEATURE:
<221> NAME/KEY: misc_feature
<222> LOCATION: (120)
<223> OTHER INFORMATION: n = a or g or c or t
<220> FEATURE:
<221> NAME/KEY: misc_feature
<222> LOCATION: (568)
<223> OTHER INFORMATION: n = a or g or c or t

<400> SEQUENCE: 3

```
tactacgtgg gttatagcag taaactgggt tttgactaag tgacatgact ggagccattc      60
tgattcttta ctgtctcacc ccatcttatt ccgttggagg atgaggatca gaggacagan    120
tgcttagttg ttttttccag agtctcaagt ctatggtctt ctgagctaca tagataggtt    180 cctttactt ggaactcctg tggaccctgg tagggttaca tattctgtga aatctttgt     240 gctaggtacg gattctgttt cagaggagga agaaagcta ttagatccat actaaggatg    300
caggcatggc agtacaaaca cctttccttc tcttttgcac gtgtgtggag aacacatatg    360
caaatgatgt caagagaaca aaacaaccat ctaaaacaga agtctggaaa atatgagtct    420
gtgtggttat tgttttttc caccgtagca gtttctttct cttttccttt gtggttttg     480 gagacagggt ttctctatgt agccctggct gtcttggagc ttacactgta gaccaggctg    540
gccttgaact cacagagatc cacctgcntc tgcctcctgt gtgggagtaa aggcgtgtac    600
caccaccaaa gtaaacactg ttgtgagtat gcatagtggg gtgtgtgtgt gtgtgtgtgc    660
tgtcagacac catcaaacaa gaaaagttag catctctcta gttgctttgg aacattcaaa    720
agctctaagc tgtgactatt aaaaaccaaa agtacctcaa gagttcttaa ctgactgcgg    780
agtttaactt cctgtctgag gggaggtgga gttagattta gtcagatcct ctcgtgggaa    840
aaaatcaaag ggactttaaa aagaaaaaa acaaaaccca acctaacagg acatcccagt     900
gtgcagttcg cgggcggctt ttgtgttgat ttccttcaca gtttccctca tctcagccac    960
tgtaggtgat gagcagcctg gcagccacca catttcgttg gaaaaagtgg aggttggatc   1020
tgcctgggca ggtgcctctc caggcttgca ggagatcccc cggtaagttt gtcagtggcc   1080
agactgcagt tgctaaggga ggctttggac agagggtgtt cgagttggca gagcctcact   1140
ttctc                                                               1145
```

<210> SEQ ID NO 4
<211> LENGTH: 32
<212> TYPE: PRT
<213> ORGANISM: Mus sp.

<400> SEQUENCE: 4

```
Met Ser Ser Leu Ala Ala Thr Thr Phe Arg Trp Lys Lys Trp Arg Leu
 1               5                  10                  15
Asp Leu Pro Gly Gln Val Pro Leu Gln Ala Cys Arg Arg Ser Pro Asp
            20                  25                  30
```

<210> SEQ ID NO 5
<211> LENGTH: 1500
<212> TYPE: DNA
<213> ORGANISM: Homo sapiens

<400> SEQUENCE: 5

```
cccagtgtgc agttcgaagg ctgcttttgt tgtccacttc ctccacatct ttttcctcat    60
catctaagca gatgtaggtg atgagcggcc tggcagccac cacgtttcat tggaaaaagt   120
gcagattgga tttgccaggg catgtagctc tccaggcttg caagcgatta ccagatgaac   180
acaatgacgt acagaagaaa acctttacca aatggataaa tgctcgattt tcaaagagtg   240
ggaaaccacc catcaatgat atgttcacag acctcaaaga tggaaggaag ctattggatc   300
ttctagaagg cctcacagga acatcactgc caaaggaacg tggttccaca agggtacatg   360
ccttaaataa cgtcaacaga gtgctgcagg ttttacatca gaacaatgtg gaattagtga   420
atatagggg aactgacatt gtggatggaa atcacaaact gactttgggg ttactttgga   480
gcatcatttt gcactggcag gtgaaagatg tcatgaagga tgtcatgtcg gacctgcagc   540
agacgaacag tgagaagatc ctgctcagct gggtgcgtca gaccaccagg ccctacagcc   600
aagtcaacgt cctcaacttc accaccagct ggacagatgg actcgccttt aatgctgtcc   660
tccaccgaca taaacctgat ctcttcagct gggataaagt tgtcaaaatg tcaccaattg   720
agagacttga acatgccttc agcaaggctc aaacttattt gggaattgaa aagctgttag   780
atcctgaaga tgttgccgtt cggcttcctg acaagaaatc cataattatg tatttaacat   840
ctttgtttga ggtgctacct cagcaagtca ccatagacgc catccgtgag gtagagacac   900
tcccaaggaa atataaaaaa gaatgtgaag aagaggcaat taatatacag agtacagcgc   960
ctgaggagga gcatgagagt ccccgagctg aaactcccag cactgtcact gaggtcgaca  1020
tggatctgga cagctatcag attgcgttgg aggaagtgct gacctggttg ctttctgctg  1080
aggacacttt ccaggagcag gatgatattt ctgatgatgt tgaagaagtc aaagaccagt  1140
ttgcaaccca tgaagctttt atgatggaac tgactgcaca ccagagcagt gtgggcagcg  1200
tcctgcaggc aggcaaccaa ctgataacac aaggaactct gtcagacgaa gaagaatttg  1260
agattcagga acagatgacc ctgctgaatg ctagatggga ggctcttagg gtggagagta  1320
tggacagaca gtcccggctg cacgatgtgc tgatggaact gcagaagaag caactgcagc  1380
agctctccgc ctggttaaca ctcacagagg agcgcattca gaagatggaa acttgccccc  1440
tggatgatga tgtaaaatct ctacaaaagc tgctagaaga acataaaagt ttgcaaagtg  1500
```

<210> SEQ ID NO 6
<211> LENGTH: 1500
<212> TYPE: DNA
<213> ORGANISM: Homo sapiens

<400> SEQUENCE: 6

```
cactttgcaa acttttatgt tcttctagca gctttttgtag agattttaca tcatcatcca    60
gggggcaagt ttccatcttc tgaatgcgct cctctgtgag tgttaaccag gcggagagct   120
```

-continued

```
gctgcagttg cttcttctgc agttccatca gcacatcgtg cagccgggac tgtctgtcca    180
tactctccac cctaagagcc tcccatctag cattcagcag ggtcatctgt tcctgaatct    240
caaattcttc ttcgtctgac agagttcctt gtgttatcag ttggttgcct gcctgcagga    300
cgctgcccac actgctctgg tgtgcagtca gttccatcat aaaagcttca tgggttgcaa    360
actggtcttt gacttcttca acatcatcag aaatatcatc ctgctcctgg aaagtgtcct    420
cagcagaaag caaccaggtc agcacttcct ccaacgcaat ctgatagctg tccagatcca    480
tgtcgacctc agtgacagtg ctgggagttt cagctcgggg actctcatgc tcctcctcag    540
gcgctgtact ctgtatatta attgcctctt cttcacattc ttttttatat ttccttggga    600
gtgtctctac ctcacggatg gcgtctatgg tgacttgctg aggtagcacc tcaaacaaag    660
atgttaaata cataattatg gatttcttgt caggaagccg aacggcaaca tcttcaggat    720
ctaacagctt ttcaattccc aaataagttt gagccttgct gaaggcatgt tcaagtctct    780
caattggtga cattttgaca actttatccc agctgaagag atcaggttta tgtcggtgga    840
ggacagcatt aaaggcgagt ccatctgtcc agctggtggt gaagttgagg acgttgactt    900
ggctgtaggg cctggtggtc tgacgcaccc agctgagcag gatcttctca ctgttcgtct    960
gctgcaggtc cgacatgaca tccttcatga catctttcac ctgccagtgc aaaatgatgc   1020
tccaaagtaa ccccaaagtc agtttgtgat ttccatccac aatgtcagtt cccctatat   1080 tcactaattc cacattgttc tgatgtaaaa cctgcagcac tctgttgacg ttatttaagg   1140
catgtaccct tgtggaacca cgttcctttg gcagtgatgt tcctgtgagg ccttctagaa   1200
gatccaatag cttccttcca tctttgaggt ctgtgaacat atcattgatg ggtggtttcc   1260
cactctttga aaatcgagca tttatccatt tggtaaaggt tttcttctgt acgtcattgt   1320
gttcatctgg taatcgcttg caagcctgga gagctacatg ccctggcaaa tccaatctgc   1380 acttttttcca atgaaacgtg gtggctgcca ggccgctcat cacctacatc tgcttagatg   1440
atgaggaaaa agatgtggag gaagtggaca acaaaagcag ccttcgaact gcacactggg   1500
```

<210> SEQ ID NO 7
<211> LENGTH: 474
<212> TYPE: PRT
<213> ORGANISM: Homo sapiens

<400> SEQUENCE: 7

```
Met Ser Gly Leu Ala Ala Thr Thr Phe His Trp Lys Lys Cys Arg Leu
 1               5                  10                  15

Asp Leu Pro Gly His Val Ala Leu Gln Ala Cys Lys Arg Leu Pro Asp
            20                  25                  30

Glu His Asn Asp Val Gln Lys Lys Thr Phe Thr Lys Trp Ile Asn Ala
        35                  40                  45

Arg Phe Ser Lys Ser Gly Lys Pro Pro Ile Asn Asp Met Phe Thr Asp
    50                  55                  60

Leu Lys Asp Gly Arg Lys Leu Leu Asp Leu Leu Glu Gly Leu Thr Gly
65                  70                  75                  80

Thr Ser Leu Pro Lys Glu Arg Gly Ser Thr Arg Val His Ala Leu Asn
                85                  90                  95

Asn Val Asn Arg Val Leu Gln Val Leu His Gln Asn Asn Val Glu Leu
            100                 105                 110

Val Asn Ile Gly Gly Thr Asp Ile Val Asp Gly Asn His Lys Leu Thr
        115                 120                 125

Leu Gly Leu Leu Trp Ser Ile Ile Leu His Trp Gln Val Lys Asp Val
```

```
                130                 135                 140
Met Lys Asp Val Met Ser Asp Leu Gln Gln Thr Asn Ser Glu Lys Ile
145                 150                 155                 160

Leu Leu Ser Trp Val Arg Gln Thr Thr Arg Pro Tyr Ser Gln Val Asn
                165                 170                 175

Val Leu Asn Phe Thr Thr Ser Trp Thr Asp Gly Leu Ala Phe Asn Ala
            180                 185                 190

Val Leu His Arg His Lys Pro Asp Leu Phe Ser Trp Asp Lys Val Val
        195                 200                 205

Lys Met Ser Pro Ile Glu Arg Leu Glu His Ala Phe Ser Lys Ala Gln
210                 215                 220

Thr Tyr Leu Gly Ile Glu Lys Leu Leu Asp Pro Glu Asp Val Ala Val
225                 230                 235                 240

Arg Leu Pro Asp Lys Lys Ser Ile Ile Met Tyr Leu Thr Ser Leu Phe
                245                 250                 255

Glu Val Leu Pro Gln Gln Val Thr Ile Asp Ala Ile Arg Glu Val Glu
            260                 265                 270

Thr Leu Pro Arg Lys Tyr Lys Lys Glu Cys Glu Glu Ala Ile Asn
        275                 280                 285

Ile Gln Ser Thr Ala Pro Glu Glu His Glu Ser Pro Arg Ala Glu
    290                 295                 300

Thr Pro Ser Thr Val Thr Glu Val Asp Met Asp Leu Asp Ser Tyr Gln
305                 310                 315                 320

Ile Ala Leu Glu Glu Val Leu Thr Trp Leu Leu Ser Ala Glu Asp Thr
                325                 330                 335

Phe Gln Glu Gln Asp Asp Ile Ser Asp Asp Val Glu Glu Val Lys Asp
            340                 345                 350

Gln Phe Ala Thr His Glu Ala Phe Met Met Glu Leu Thr Ala His Gln
        355                 360                 365

Ser Ser Val Gly Ser Val Leu Gln Ala Gly Asn Gln Leu Ile Thr Gln
    370                 375                 380

Gly Thr Leu Ser Asp Glu Glu Phe Glu Ile Gln Glu Gln Met Thr
385                 390                 395                 400

Leu Leu Asn Ala Arg Trp Glu Ala Leu Arg Val Glu Ser Met Asp Arg
                405                 410                 415

Gln Ser Arg Leu His Asp Val Leu Met Glu Leu Gln Lys Lys Gln Leu
            420                 425                 430

Gln Gln Leu Ser Ala Trp Leu Thr Leu Thr Glu Glu Arg Ile Gln Lys
        435                 440                 445

Met Glu Thr Cys Pro Leu Asp Asp Asp Val Lys Ser Leu Gln Lys Leu
450                 455                 460

Leu Glu Glu His Lys Ser Leu Gln Ser Asp
465                 470

<210> SEQ ID NO 8
<211> LENGTH: 6059
<212> TYPE: DNA
<213> ORGANISM: Artificial Sequence
<220> FEATURE:
<221> NAME/KEY: CDS
<222> LOCATION: (11)..(6052)
<220> FEATURE:
<223> OTHER INFORMATION: Description of Artificial Sequence: Utrophin B
      isoform "minigene"

<400> SEQUENCE: 8
```

-continued

```
actagtcaag atg agc ggc ctg gca gcc acc acg ttt cat tgg aaa aag        49
          Met Ser Gly Leu Ala Ala Thr Thr Phe His Trp Lys Lys
            1               5                  10 tgc aga ttg gat ttg cca ggg cat gta gct ctc cag gct tgc aag cga       97
Cys Arg Leu Asp Leu Pro Gly His Val Ala Leu Gln Ala Cys Lys Arg
 15                  20                  25 tta cca gat gaa cac aat gat gta cag aag aaa acc ttt acc aaa tgg      145
Leu Pro Asp Glu His Asn Asp Val Gln Lys Lys Thr Phe Thr Lys Trp
 30                  35                  40                  45 ata aac gct cga ttt tcc aag agt ggg aaa cca ccc atc agt gat atg      193
Ile Asn Ala Arg Phe Ser Lys Ser Gly Lys Pro Pro Ile Ser Asp Met
                50                  55                  60 ttc tca gac ctc aaa gat ggg aga aag ctc ttg gat ctt ctc gaa ggc      241
Phe Ser Asp Leu Lys Asp Gly Arg Lys Leu Leu Asp Leu Leu Glu Gly
                 65                  70                  75 ctc aca gga aca tca ttg cca aag gaa cgt ggt tcc aca agg gtg cat      289
Leu Thr Gly Thr Ser Leu Pro Lys Glu Arg Gly Ser Thr Arg Val His
             80                  85                  90 gcc tta aac aat gtc aac cga gtg cta cag gtt tta cat cag aac aat      337
Ala Leu Asn Asn Val Asn Arg Val Leu Gln Val Leu His Gln Asn Asn
 95                 100                 105 gtg gac ttg gtg aat att gga ggc acg gac att gtg gct gga aat ccc      385
Val Asp Leu Val Asn Ile Gly Gly Thr Asp Ile Val Ala Gly Asn Pro
110                 115                 120                 125 aag ctg act tta ggg tta ctc tgg agc atc att ctg cac tgg cag gtg      433
Lys Leu Thr Leu Gly Leu Leu Trp Ser Ile Ile Leu His Trp Gln Val
                130                 135                 140 aag gat gtc atg aaa gat atc atg tca gac ctg cag cag aca aac agc      481
Lys Asp Val Met Lys Asp Ile Met Ser Asp Leu Gln Gln Thr Asn Ser
                145                 150                 155 gag aag atc ctg ctg agc tgg gtg cgg cag acc acc agg ccc tac agt      529
Glu Lys Ile Leu Leu Ser Trp Val Arg Gln Thr Thr Arg Pro Tyr Ser
                160                 165                 170 caa gtc aac gtc ctc aac ttc acc acc agc tgg acc gat gga ctc gcg      577
Gln Val Asn Val Leu Asn Phe Thr Thr Ser Trp Thr Asp Gly Leu Ala
175                 180                 185 ttc aac gcc gtg ctc cac cgg cac aaa cca gat ctc ttc gac tgg gac      625
Phe Asn Ala Val Leu His Arg His Lys Pro Asp Leu Phe Asp Trp Asp
190                 195                 200                 205 gag atg gtc aaa atg tcc cca att gag aga ctt gac cat gct ttt gac      673
Glu Met Val Lys Met Ser Pro Ile Glu Arg Leu Asp His Ala Phe Asp
                210                 215                 220 aag gcc cac act tct ttg gga att gaa aag ctc cta agt cct gaa act      721
Lys Ala His Thr Ser Leu Gly Ile Glu Lys Leu Leu Ser Pro Glu Thr
                225                 230                 235 gtt gct gtg cat ctc cct gac aag aaa tcc ata att atg tat tta acg      769
Val Ala Val His Leu Pro Asp Lys Lys Ser Ile Ile Met Tyr Leu Thr
                240                 245                 250 tct ctg ttt gag gtg ctt cct cag caa gtc acg ata gat gcc atc cga      817
Ser Leu Phe Glu Val Leu Pro Gln Gln Val Thr Ile Asp Ala Ile Arg
                255                 260                 265 gag gtg gag act ctc cca agg aag tat aag aaa gaa tgt gaa gag gaa      865
Glu Val Glu Thr Leu Pro Arg Lys Tyr Lys Lys Glu Cys Glu Glu Glu
270                 275                 280                 285 gaa att cat atc cag agt gca gtg ctg gca gag gaa ggc cag agt ccc      913
Glu Ile His Ile Gln Ser Ala Val Leu Ala Glu Glu Gly Gln Ser Pro
                290                 295                 300 cga gct gag acc cct agc acc gtc act gaa gtg gac atg gat ttg gac      961
Arg Ala Glu Thr Pro Ser Thr Val Thr Glu Val Asp Met Asp Leu Asp
                305                 310                 315
```

-continued

| | |
|---|---|
| agc tac cag ata gcg cta gag gaa gtg ctg acg tgg ctg ctg tcc gcg<br>Ser Tyr Gln Ile Ala Leu Glu Glu Val Leu Thr Trp Leu Leu Ser Ala<br>    320                       325                 330 | 1009 |
| gag gac acg ttc cag gag caa cat gac att tct gat gat gtc gaa gaa<br>Glu Asp Thr Phe Gln Glu Gln His Asp Ile Ser Asp Asp Val Glu Glu<br>335                     340                     345 | 1057 |
| gtc aaa gag cag ttt gct acc cat gaa act ttt atg atg gag ctg aca<br>Val Lys Glu Gln Phe Ala Thr His Glu Thr Phe Met Met Glu Leu Thr<br>350                   355                   360              365 | 1105 |
| gca cac cag agc agc gtg ggg agc gtc ctg cag gct ggc aac cag ctg<br>Ala His Gln Ser Ser Val Gly Ser Val Leu Gln Ala Gly Asn Gln Leu<br>               370                   375                 380 | 1153 |
| atg aca caa ggg act ctg tcc aga gag gag gag ttt gag atc cag gaa<br>Met Thr Gln Gly Thr Leu Ser Arg Glu Glu Glu Phe Glu Ile Gln Glu<br>385                     390                     395 | 1201 |
| cag atg acc ttg ctg aat gca agg tgg gag gcg ctc cgg gtg gag agc<br>Gln Met Thr Leu Leu Asn Ala Arg Trp Glu Ala Leu Arg Val Glu Ser<br>        400                   405                 410 | 1249 |
| atg gag agg cag tcc cgg ctg cac gac gct ctg atg gag ctg cag aag<br>Met Glu Arg Gln Ser Arg Leu His Asp Ala Leu Met Glu Leu Gln Lys<br>415                     420                     425 | 1297 |
| aaa cag ctg cag cag ctc tca agc tgg ctg gcc ctc aca gaa gag cgc<br>Lys Gln Leu Gln Gln Leu Ser Ser Trp Leu Ala Leu Thr Glu Glu Arg<br>430                     435                   440              445 | 1345 |
| att cag aag atg gag agc ctc ccg ctg ggt gat gac ctg ccc tcc ctg<br>Ile Gln Lys Met Glu Ser Leu Pro Leu Gly Asp Asp Leu Pro Ser Leu<br>               450                   455                 460 | 1393 |
| cag aag ctg ctt caa gaa cat aaa agt ttg caa aat gac ctt gaa gct<br>Gln Lys Leu Leu Gln Glu His Lys Ser Leu Gln Asn Asp Leu Glu Ala<br>465                     470                     475 | 1441 |
| gaa cag gtg aag gta aat tcc tta act cac atg gtg gtg att gtg gat<br>Glu Gln Val Lys Val Asn Ser Leu Thr His Met Val Val Ile Val Asp<br>        480                   485                 490 | 1489 |
| gaa aac agt ggg gag agt gcc aca gct ctt ctg gaa gat cag tta cag<br>Glu Asn Ser Gly Glu Ser Ala Thr Ala Leu Leu Glu Asp Gln Leu Gln<br>495                     500                     505 | 1537 |
| aaa ctg ggt gag cgc tgg aca gct gta tgc cgc tgg act gaa gaa cgt<br>Lys Leu Gly Glu Arg Trp Thr Ala Val Cys Arg Trp Thr Glu Glu Arg<br>510                     515                   520              525 | 1585 |
| tgg aac agg ttg caa gaa atc agt att ctg tgg cag gaa tta ttt gaa<br>Trp Asn Arg Leu Gln Glu Ile Ser Ile Leu Trp Gln Glu Leu Leu Glu<br>               530                   535                 540 | 1633 |
| gag cag tgt ctg ttg gag gct tgg ctc acc gaa aag gaa gag gct ttg<br>Glu Gln Cys Leu Leu Glu Ala Trp Leu Thr Glu Lys Glu Glu Ala Leu<br>545                     550                     555 | 1681 |
| gat aaa gtt caa acc agc aac ttt aaa gac cag aag gaa cta agt gtc<br>Asp Lys Val Gln Thr Ser Asn Phe Lys Asp Gln Lys Glu Leu Ser Val<br>        560                   565                 570 | 1729 |
| agt gtc cgg cgt ctg gct ata ttg aag gaa gac atg gaa atg aag agg<br>Ser Val Arg Arg Leu Ala Ile Leu Lys Glu Asp Met Glu Met Lys Arg<br>575                     580                   585 | 1777 |
| cag act ctg gat caa ctg agt gag att ggc cag gat gtg ggc caa tta<br>Gln Thr Leu Asp Gln Leu Ser Glu Ile Gly Gln Asp Val Gly Gln Leu<br>590                     595                   600              605 | 1825 |
| ctc agt aat ccc aag gca tct aag aag atg aac agt gac tct gag gag<br>Leu Ser Asn Pro Lys Ala Ser Lys Lys Met Asn Ser Asp Ser Glu Glu<br>               610                   615                 620 | 1873 |
| cta aca cag aga tgg gat tct ctg gtt cag aga ctc gaa gac tct tct<br>Leu Thr Gln Arg Trp Asp Ser Leu Val Gln Arg Leu Glu Asp Ser Ser | 1921 |

-continued

|  |  |  |  |
|---|---|---|---|
| | 625 | 630 | 635 |

```
aac cag gtg act cag gcg gta gcg aag ctc ggc atg tcc cag att cca    1969
Asn Gln Val Thr Gln Ala Val Ala Lys Leu Gly Met Ser Gln Ile Pro
        640             645                 650 cag aag gac cta ttg gag acc gtt cat gtg aga gaa caa ggg atg gtg    2017
Gln Lys Asp Leu Leu Glu Thr Val His Val Arg Glu Gln Gly Met Val
    655             660                 665 aag aag ccc aag cag gaa ctg cct cct ccg tta aca aag gct gag cat    2065
Lys Lys Pro Lys Gln Glu Leu Pro Pro Pro Leu Thr Lys Ala Glu His
670             675                 680                 685 gct atg caa aag aga tca acc acc gaa ttg gga gaa aac ctg caa gaa    2113
Ala Met Gln Lys Arg Ser Thr Thr Glu Leu Gly Glu Asn Leu Gln Glu
                690                 695                 700 tta aga gac tta act caa gaa atg gaa gta cat gct gaa aaa ctc aaa    2161
Leu Arg Asp Leu Thr Gln Glu Met Glu Val His Ala Glu Lys Leu Lys
            705                 710                 715 tgg ctg aat aga act gaa ttg gag atg ctt tca gat aaa agt ctg agt    2209
Trp Leu Asn Arg Thr Glu Leu Glu Met Leu Ser Asp Lys Ser Leu Ser
        720                 725                 730 tta cct gaa agg gat aaa att tca gaa agc tta agg act gta aat atg    2257
Leu Pro Glu Arg Asp Lys Ile Ser Glu Ser Leu Arg Thr Val Asn Met
    735                 740                 745 aca tgg aat aag att tgc aga gag gtg cct acc acc ctg aag gaa tgc    2305
Thr Trp Asn Lys Ile Cys Arg Glu Val Pro Thr Thr Leu Lys Glu Cys
750                 755                 760                 765 atc cag gag ccc agt tct gtt tca cag aca agg att gct gct cat cct    2353
Ile Gln Glu Pro Ser Ser Val Ser Gln Thr Arg Ile Ala Ala His Pro
                770                 775                 780 aat gtc caa aag gtg gtg cta gta tca tct gcg tca gat att cct gtt    2401
Asn Val Gln Lys Val Val Leu Val Ser Ser Ala Ser Asp Ile Pro Val
            785                 790                 795 cag tct cat cgt act tcg gaa att tca att cct gct gat ctt gat aaa    2449
Gln Ser His Arg Thr Ser Glu Ile Ser Ile Pro Ala Asp Leu Asp Lys
        800                 805                 810 act ata aca gaa cta gcc gac tgg ctg gta tta atc gac cag atg ctg    2497
Thr Ile Thr Glu Leu Ala Asp Trp Leu Val Leu Ile Asp Gln Met Leu
    815                 820                 825 aag tcc aac att gtc act gtt ggg gat gta gaa gag atc aat aag acc    2545
Lys Ser Asn Ile Val Thr Val Gly Asp Val Glu Glu Ile Asn Lys Thr
830                 835                 840                 845 gtt tcc cga atg aaa att aca aag gct gac tta gaa cag cgc cat cct    2593
Val Ser Arg Met Lys Ile Thr Lys Ala Asp Leu Glu Gln Arg His Pro
                850                 855                 860 cag ctg gat tat gtt ttt aca ttg gca cag aat ttg aaa aat aaa gct    2641
Gln Leu Asp Tyr Val Phe Thr Leu Ala Gln Asn Leu Lys Asn Lys Ala
            865                 870                 875 tcc agt tca gat atg aga aca gca att aca gaa aaa ttg gaa agg gtc    2689
Ser Ser Ser Asp Met Arg Thr Ala Ile Thr Glu Lys Leu Glu Arg Val
        880                 885                 890 aag aac cag tgg gat ggc acc cag cat ggc gtt gag cta aga cag cag    2737
Lys Asn Gln Trp Asp Gly Thr Gln His Gly Val Glu Leu Arg Gln Gln
    895                 900                 905 cag ctt gag gac atg att att gac agt ctt cag tgg gat gac cat agg    2785
Gln Leu Glu Asp Met Ile Ile Asp Ser Leu Gln Trp Asp Asp His Arg
910                 915                 920                 925 gag gag act gaa gaa ctg atg aga aaa tat gag gct cga ctc tat att    2833
Glu Glu Thr Glu Glu Leu Met Arg Lys Tyr Glu Ala Arg Leu Tyr Ile
                930                 935                 940 ctt cag caa gcc cga cgg gat cca ctc acc aaa caa att tct gat aac    2881
```

```
Leu Gln Gln Ala Arg Arg Asp Pro Leu Thr Lys Gln Ile Ser Asp Asn
            945                 950                 955 caa ata ctg ctt caa gaa ctg ggt cct gga gat ggt atc gtc atg gcg       2929
Gln Ile Leu Leu Gln Glu Leu Gly Pro Gly Asp Gly Ile Val Met Ala
            960                 965                 970 ttc gat aac gtc ctg cag aaa ctc ctg gag gaa tat ggg agt gat gac       2977
Phe Asp Asn Val Leu Gln Lys Leu Leu Glu Glu Tyr Gly Ser Asp Asp
            975                 980                 985 aca agg aat gtg aaa gaa acc aca gag tac tta aaa aca tca tgg atc       3025
Thr Arg Asn Val Lys Glu Thr Thr Glu Tyr Leu Lys Thr Ser Trp Ile
990                 995                 1000                1005 aat ctc aaa caa agt att gct gac aga cag aac gcc ttg gag gct gag       3073
Asn Leu Lys Gln Ser Ile Ala Asp Arg Gln Asn Ala Leu Glu Ala Glu
                1010                1015                1020 tgg agg acg gtg cag gcc tct cgc aga gat ctg gaa aac ttc ctg aag       3121
Trp Arg Thr Val Gln Ala Ser Arg Arg Asp Leu Glu Asn Phe Leu Lys
                1025                1030                1035 tgg atc caa gaa gca gag acc aca gtg aat gtg ctt gtg gat gcc tct       3169
Trp Ile Gln Glu Ala Glu Thr Thr Val Asn Val Leu Val Asp Ala Ser
                1040                1045                1050 cat cgg gag aat gct ctt cag gat agt atc ttg gcc agg gaa ctc aaa       3217
His Arg Glu Asn Ala Leu Gln Asp Ser Ile Leu Ala Arg Glu Leu Lys
                1055                1060                1065 cag cag atg cag gac atc cag gca gaa att gat gcc cac aat gac ata       3265
Gln Gln Met Gln Asp Ile Gln Ala Glu Ile Asp Ala His Asn Asp Ile
1070                1075                1080                1085 ttt aaa agc att gac gga aac agg cag aag atg gta aaa gct ttg gga       3313
Phe Lys Ser Ile Asp Gly Asn Arg Gln Lys Met Val Lys Ala Leu Gly
                1090                1095                1100 aat tct gaa gag gct act atg ctt caa cat cga ctg gat gat atg aac       3361
Asn Ser Glu Glu Ala Thr Met Leu Gln His Arg Leu Asp Asp Met Asn
                1105                1110                1115 caa aga tgg aat gac tta aaa gca aaa tct gct agc atc agg gcc cat       3409
Gln Arg Trp Asn Asp Leu Lys Ala Lys Ser Ala Ser Ile Arg Ala His
                1120                1125                1130 ttg gag gcc agc gct gag aag tgg aac agg ttg ctg atg tcc tta gaa       3457
Leu Glu Ala Ser Ala Glu Lys Trp Asn Arg Leu Leu Met Ser Leu Glu
                1135                1140                1145 gaa ctg atc aaa tgg ctg aat atg aaa gat gaa gag ctt aag aaa caa       3505
Glu Leu Ile Lys Trp Leu Asn Met Lys Asp Glu Glu Leu Lys Lys Gln
1150                1155                1160                1165 atg cct att gga gga gat gtt cca gcc tta cag ctc cag tat gac cat       3553
Met Pro Ile Gly Gly Asp Val Pro Ala Leu Gln Leu Gln Tyr Asp His
                1170                1175                1180 tgt aag gcc ctg aga cgg gag tta aag gag aaa gaa tat tct gtc ctg       3601
Cys Lys Ala Leu Arg Arg Glu Leu Lys Glu Lys Glu Tyr Ser Val Leu
                1185                1190                1195 aat gct gtc gac cag gcc cga gtt ttc ttg gct gat cag cca att gag       3649
Asn Ala Val Asp Gln Ala Arg Val Phe Leu Ala Asp Gln Pro Ile Glu
                1200                1205                1210 gcc cct gaa gag cca aga aga aac cta caa tca aaa aca gaa tta act       3697
Ala Pro Glu Glu Pro Arg Arg Asn Leu Gln Ser Lys Thr Glu Leu Thr
            1215                1220                1225 cct gag gag aga gcc caa aag att gcc aaa gcc atg cgc aaa cag tct       3745
Pro Glu Glu Arg Ala Gln Lys Ile Ala Lys Ala Met Arg Lys Gln Ser
1230                1235                1240                1245 tct gaa gtc aaa gaa aaa tgg gaa agt cta aat gct gta act agc aat       3793
Ser Glu Val Lys Glu Lys Trp Glu Ser Leu Asn Ala Val Thr Ser Asn
                1250                1255                1260
```

-continued

```
tgg caa aag caa gtg gac aag gca ttg gag aaa ctc aga gac ctg cag      3841
Trp Gln Lys Gln Val Asp Lys Ala Leu Glu Lys Leu Arg Asp Leu Gln
        1265                1270                1275 gga gct atg gat gac ctg gac gct gac atg aag gag gca gag tcc gtg      3889
Gly Ala Met Asp Asp Leu Asp Ala Asp Met Lys Glu Ala Glu Ser Val
    1280                1285                1290 cgg aat ggc tgg aag ccc gtg gga gac tta ctc att gac tcg ctg cag      3937
Arg Asn Gly Trp Lys Pro Val Gly Asp Leu Leu Ile Asp Ser Leu Gln
1295                1300                1305 gat cac att gaa aaa atc atg gca ttt aga gaa gaa att gca cca atc      3985
Asp His Ile Glu Lys Ile Met Ala Phe Arg Glu Glu Ile Ala Pro Ile
1310                1315                1320                1325 aac ttt aaa gtt aaa acg gtg aat gat tta tcc agt cag ctg tct cca      4033
Asn Phe Lys Val Lys Thr Val Asn Asp Leu Ser Ser Gln Leu Ser Pro
        1330                1335                1340 ctt gac ctg cat ccc tct cta aag atg tct cgc cag cta gat gac ctt      4081
Leu Asp Leu His Pro Ser Leu Lys Met Ser Arg Gln Leu Asp Asp Leu
    1345                1350                1355 aat atg cga tgg aaa ctt tta cag gtt tct gtg gat gat cgc ctt aaa      4129
Asn Met Arg Trp Lys Leu Leu Gln Val Ser Val Asp Asp Arg Leu Lys
1360                1365                1370 cag ctt cag gaa gcc cac aga gat ttt gga cca tcc tct cag cat ttt      4177
Gln Leu Gln Glu Ala His Arg Asp Phe Gly Pro Ser Ser Gln His Phe
1375                1380                1385 ctc tct acg tca gtc cag ctg ccg tgg caa aga tcc att tca cat aat      4225
Leu Ser Thr Ser Val Gln Leu Pro Trp Gln Arg Ser Ile Ser His Asn
1390                1395                1400                1405 aaa gtg ccc tat tac atc aac cat caa aca cag acc acc tgt tgg gac      4273
Lys Val Pro Tyr Tyr Ile Asn His Gln Thr Gln Thr Thr Cys Trp Asp
        1410                1415                1420 cat cct aaa atg acc gaa ctc ttt caa tcc ctt gct gac ctg aat aat      4321
His Pro Lys Met Thr Glu Leu Phe Gln Ser Leu Ala Asp Leu Asn Asn
    1425                1430                1435 gta cgt ttt tct gcc tac cgt aca gca atc aaa atc cga aga cta caa      4369
Val Arg Phe Ser Ala Tyr Arg Thr Ala Ile Lys Ile Arg Arg Leu Gln
1440                1445                1450 aaa gca cta tgt ttg gat ctc tta gag ttg agt aca aca aat gaa att      4417
Lys Ala Leu Cys Leu Asp Leu Leu Glu Leu Ser Thr Thr Asn Glu Ile
1455                1460                1465 ttc aaa cag cac aag ttg aac caa aat gac cag ctc ctc agt gtt cca      4465
Phe Lys Gln His Lys Leu Asn Gln Asn Asp Gln Leu Leu Ser Val Pro
1470                1475                1480                1485 gat gtc atc aac tgt ctg aca aca act tat gat gga ctt gag caa atg      4513
Asp Val Ile Asn Cys Leu Thr Thr Thr Tyr Asp Gly Leu Glu Gln Met
        1490                1495                1500 cat aag gac ctg gtc aac gtt cca ctc tgt gtt gat atg tgt ctc aat      4561
His Lys Asp Leu Val Asn Val Pro Leu Cys Val Asp Met Cys Leu Asn
    1505                1510                1515 tgg ttg ctc aat gtc tat gac acg ggt cga act gga aaa att aga gtg      4609
Trp Leu Leu Asn Val Tyr Asp Thr Gly Arg Thr Gly Lys Ile Arg Val
1520                1525                1530 cag agt ctg aag att gga tta atg tct ctc tcc aaa ggt ctc ttg gaa      4657
Gln Ser Leu Lys Ile Gly Leu Met Ser Leu Ser Lys Gly Leu Leu Glu
1535                1540                1545 gaa aaa tac aga tat ctc ttt aag gaa gtt gcg ggg ccg aca gaa atg      4705
Glu Lys Tyr Arg Tyr Leu Phe Lys Glu Val Ala Gly Pro Thr Glu Met
1550                1555                1560                1565 tgt gac cag agg cag ctg ggc ctg tta ctt cat gat gcc atc cag atc      4753
Cys Asp Gln Arg Gln Leu Gly Leu Leu Leu His Asp Ala Ile Gln Ile
        1570                1575                1580
```

-continued

| | |
|---|---|
| ccc cgg cag cta ggt gaa gta gca gct ttt gga ggc agt aat att gag<br>Pro Arg Gln Leu Gly Glu Val Ala Ala Phe Gly Gly Ser Asn Ile Glu<br>1585                     1590                      1595 | 4801 |
| cct agt gtt cgc agc tgc ttc caa cag aat aac aat aaa cca gaa ata<br>Pro Ser Val Arg Ser Cys Phe Gln Gln Asn Asn Asn Lys Pro Glu Ile<br>    1600                    1605                    1610 | 4849 |
| agt gtg aaa gag ttt ata gat tgg atg cat ttg gaa cca cag tcc atg<br>Ser Val Lys Glu Phe Ile Asp Trp Met His Leu Glu Pro Gln Ser Met<br>1615                     1620                      1625 | 4897 |
| gtt tgg ctc cca gtt tta cat cga gtg gca gca gcg gag act gca aaa<br>Val Trp Leu Pro Val Leu His Arg Val Ala Ala Ala Glu Thr Ala Lys<br>1630                     1635                     1640                    1645 | 4945 |
| cat cag gcc aaa tgc aac atc tgt aaa gaa tgt cca att gtc ggg ttc<br>His Gln Ala Lys Cys Asn Ile Cys Lys Glu Cys Pro Ile Val Gly Phe<br>           1650                    1655                    1660 | 4993 |
| agg tat aga agc ctt aag cat ttt aac tat gat gtc tgc cag agt tgt<br>Arg Tyr Arg Ser Leu Lys His Phe Asn Tyr Asp Val Cys Gln Ser Cys<br>1665                     1670                      1675 | 5041 |
| ttc ttt tcg ggt cga aca gca aaa ggt cac aaa tta cat tac cca atg<br>Phe Phe Ser Gly Arg Thr Ala Lys Gly His Lys Leu His Tyr Pro Met<br>           1680                    1685                    1690 | 5089 |
| gtg gaa tat tgt ata cct aca aca tct ggg gaa gat gta cga gac ttc<br>Val Glu Tyr Cys Ile Pro Thr Thr Ser Gly Glu Asp Val Arg Asp Phe<br>1695                     1700                      1705 | 5137 |
| aca aag gta ctt aag aac aag ttc agg tcg aag aag tac ttt gcc aaa<br>Thr Lys Val Leu Lys Asn Lys Phe Arg Ser Lys Lys Tyr Phe Ala Lys<br>1710                     1715                     1720                    1725 | 5185 |
| cac cct cga ctt ggt tac ctg cct gtc cag aca gtt ctt gaa ggt gac<br>His Pro Arg Leu Gly Tyr Leu Pro Val Gln Thr Val Leu Glu Gly Asp<br>           1730                    1735                    1740 | 5233 |
| aac tta gag act cct atc aca ctc atc agt atg tgg cca gag cac tat<br>Asn Leu Glu Thr Pro Ile Thr Leu Ile Ser Met Trp Pro Glu His Tyr<br>                   1745                    1750                    1755 | 5281 |
| gac ccc tca caa tct cct caa ctg ttt cat gat gac acc cat tca aga<br>Asp Pro Ser Gln Ser Pro Gln Leu Phe His Asp Asp Thr His Ser Arg<br>    1760                    1765                    1770 | 5329 |
| ata gaa caa tat gcc aca cga ctg gcc cag atg gaa agg act aat ggg<br>Ile Glu Gln Tyr Ala Thr Arg Leu Ala Gln Met Glu Arg Thr Asn Gly<br>1775                     1780                      1785 | 5377 |
| tct ttt ctc act gat agc agc tcc acc aca gga agt gtg gaa gac gag<br>Ser Phe Leu Thr Asp Ser Ser Ser Thr Thr Gly Ser Val Glu Asp Glu<br>1790                     1795                     1800                    1805 | 5425 |
| cac gcc ctc atc cag cag tat tgc caa aca ctc gga gga gag tcc cca<br>His Ala Leu Ile Gln Gln Tyr Cys Gln Thr Leu Gly Gly Glu Ser Pro<br>                   1810                    1815                    1820 | 5473 |
| gtg agc cag ccg cag agc cca gct cag atc ctg aag tca gta gag agg<br>Val Ser Gln Pro Gln Ser Pro Ala Gln Ile Leu Lys Ser Val Glu Arg<br>    1825                    1830                    1835 | 5521 |
| gaa gaa cgt gga gaa ctg gag agg atc att gct gac ctg gag gaa gaa<br>Glu Glu Arg Gly Glu Leu Glu Arg Ile Ile Ala Asp Leu Glu Glu Glu<br>1840                     1845                      1850 | 5569 |
| caa aga aat cta cag gtg gag tat gag cag ctg aag gac cag cac ctc<br>Gln Arg Asn Leu Gln Val Glu Tyr Glu Gln Leu Lys Asp Gln His Leu<br>1855                     1860                      1865 | 5617 |
| cga agg ggg ctc cct gtc ggt tca ccg cca gag tcg att ata tct ccc<br>Arg Arg Gly Leu Pro Val Gly Ser Pro Pro Glu Ser Ile Ile Ser Pro<br>1870                     1875                     1880                    1885 | 5665 |
| cat cac acg tct gag gat tca gaa ctt ata gca gaa gca aaa ctc ctc<br>His His Thr Ser Glu Asp Ser Glu Leu Ile Ala Glu Ala Lys Leu Leu | 5713 |

-continued

```
                  1890                1895                1900
agg cag cac aaa ggt cgg ctg gag gct agg atg cag att tta gaa gat    5761
Arg Gln His Lys Gly Arg Leu Glu Ala Arg Met Gln Ile Leu Glu Asp
            1905                1910                1915 cac aat aaa cag ctg gag tct cag ctc cac cgc ctc cga cag ctg ctg    5809
His Asn Lys Gln Leu Glu Ser Gln Leu His Arg Leu Arg Gln Leu Leu
        1920                1925                1930 gag cag cct gaa tct gat tcc cga atc aat ggt gtt tcc cca tgg gct    5857
Glu Gln Pro Glu Ser Asp Ser Arg Ile Asn Gly Val Ser Pro Trp Ala
    1935                1940                1945 tct cct cag cat tct gca ctg agc tac tcg ctt gat cca gat gcc tcc    5905
Ser Pro Gln His Ser Ala Leu Ser Tyr Ser Leu Asp Pro Asp Ala Ser
1950                1955                1960                1965 ggc cca cag ttc cac cag gca gcg gga gag gac ctg ctg gcc cca ccg    5953
Gly Pro Gln Phe His Gln Ala Ala Gly Glu Asp Leu Leu Ala Pro Pro
            1970                1975                1980 cac gac acc agc acg gat ctc acg gag gtc atg gag cag att cac agc    6001
His Asp Thr Ser Thr Asp Leu Thr Glu Val Met Glu Gln Ile His Ser
        1985                1990                1995 acg ttt cca tct tgc tgc cca aat gtt ccc agc agg cca cag gca atg    6049
Thr Phe Pro Ser Cys Cys Pro Asn Val Pro Ser Arg Pro Gln Ala Met
    2000                2005                2010 taa tcactag                                                         6059
```

<210> SEQ ID NO 9
<211> LENGTH: 2013
<212> TYPE: PRT
<213> ORGANISM: Artificial Sequence
<220> FEATURE:
<223> OTHER INFORMATION: Description of Artificial Sequence: Predicted
      amino acid sequence of a utrophin B isoform "minigene"

<400> SEQUENCE: 9

```
Met Ser Gly Leu Ala Ala Thr Thr Phe His Trp Lys Lys Cys Arg Leu
  1               5                  10                  15

Asp Leu Pro Gly His Val Ala Leu Gln Ala Cys Lys Arg Leu Pro Asp
             20                  25                  30

Glu His Asn Asp Val Gln Lys Lys Thr Phe Thr Lys Trp Ile Asn Ala
         35                  40                  45

Arg Phe Ser Lys Ser Gly Lys Pro Pro Ile Ser Asp Met Phe Ser Asp
     50                  55                  60

Leu Lys Asp Gly Arg Lys Leu Leu Asp Leu Leu Glu Gly Leu Thr Gly
 65                  70                  75                  80

Thr Ser Leu Pro Lys Glu Arg Gly Ser Thr Arg Val His Ala Leu Asn
                 85                  90                  95

Asn Val Asn Arg Val Leu Gln Val Leu His Gln Asn Asn Val Asp Leu
            100                 105                 110

Val Asn Ile Gly Gly Thr Asp Ile Val Ala Gly Asn Pro Lys Leu Thr
        115                 120                 125

Leu Gly Leu Leu Trp Ser Ile Ile Leu His Trp Gln Val Lys Asp Val
    130                 135                 140

Met Lys Asp Ile Met Ser Asp Leu Gln Gln Thr Asn Ser Glu Lys Ile
145                 150                 155                 160

Leu Leu Ser Trp Val Arg Gln Thr Thr Arg Pro Tyr Ser Gln Val Asn
                165                 170                 175

Val Leu Asn Phe Thr Thr Ser Trp Thr Asp Gly Leu Ala Phe Asn Ala
            180                 185                 190
```

```
Val Leu His Arg His Lys Pro Asp Leu Phe Asp Trp Asp Glu Met Val
            195                 200                 205

Lys Met Ser Pro Ile Glu Arg Leu Asp His Ala Phe Asp Lys Ala His
            210                 215                 220

Thr Ser Leu Gly Ile Glu Lys Leu Leu Ser Pro Glu Thr Val Ala Val
225                 230                 235                 240

His Leu Pro Asp Lys Lys Ser Ile Ile Met Tyr Leu Thr Ser Leu Phe
            245                 250                 255

Glu Val Leu Pro Gln Gln Val Thr Ile Asp Ala Ile Arg Glu Val Glu
            260                 265                 270

Thr Leu Pro Arg Lys Tyr Lys Lys Glu Cys Glu Glu Glu Ile His
            275                 280                 285

Ile Gln Ser Ala Val Leu Ala Glu Glu Gly Gln Ser Pro Arg Ala Glu
            290                 295                 300

Thr Pro Ser Thr Val Thr Glu Val Asp Met Asp Leu Asp Ser Tyr Gln
305                 310                 315                 320

Ile Ala Leu Glu Glu Val Leu Thr Trp Leu Leu Ser Ala Glu Asp Thr
            325                 330                 335

Phe Gln Glu Gln His Asp Ile Ser Asp Val Glu Glu Val Lys Glu
            340                 345                 350

Gln Phe Ala Thr His Glu Thr Phe Met Met Glu Leu Thr Ala His Gln
            355                 360                 365

Ser Ser Val Gly Ser Val Leu Gln Ala Gly Asn Gln Leu Met Thr Gln
            370                 375                 380

Gly Thr Leu Ser Arg Glu Glu Glu Phe Glu Ile Gln Glu Gln Met Thr
385                 390                 395                 400

Leu Leu Asn Ala Arg Trp Glu Ala Leu Arg Val Glu Ser Met Glu Arg
            405                 410                 415

Gln Ser Arg Leu His Asp Ala Leu Met Glu Leu Gln Lys Lys Gln Leu
            420                 425                 430

Gln Gln Leu Ser Ser Trp Leu Ala Leu Thr Glu Glu Arg Ile Gln Lys
            435                 440                 445

Met Glu Ser Leu Pro Leu Gly Asp Asp Leu Pro Ser Leu Gln Lys Leu
            450                 455                 460

Leu Gln Glu His Lys Ser Leu Gln Asn Asp Leu Glu Ala Glu Gln Val
465                 470                 475                 480

Lys Val Asn Ser Leu Thr His Met Val Val Ile Val Asp Glu Asn Ser
            485                 490                 495

Gly Glu Ser Ala Thr Ala Leu Leu Glu Asp Gln Leu Gln Lys Leu Gly
            500                 505                 510

Glu Arg Trp Thr Ala Val Cys Arg Trp Thr Glu Arg Trp Asn Arg
            515                 520                 525

Leu Gln Glu Ile Ser Ile Leu Trp Gln Glu Leu Leu Glu Glu Gln Cys
            530                 535                 540

Leu Leu Glu Ala Trp Leu Thr Glu Lys Glu Glu Ala Leu Asp Lys Val
545                 550                 555                 560

Gln Thr Ser Asn Phe Lys Asp Gln Lys Glu Leu Ser Val Ser Val Arg
            565                 570                 575

Arg Leu Ala Ile Leu Lys Glu Asp Met Glu Met Lys Arg Gln Thr Leu
            580                 585                 590

Asp Gln Leu Ser Glu Ile Gly Gln Asp Val Gly Gln Leu Leu Ser Asn
            595                 600                 605

Pro Lys Ala Ser Lys Lys Met Asn Ser Asp Ser Glu Glu Leu Thr Gln
```

-continued

```
            610                 615                 620
Arg Trp Asp Ser Leu Val Gln Arg Leu Glu Asp Ser Ser Asn Gln Val
625                 630                 635                 640

Thr Gln Ala Val Ala Lys Leu Gly Met Ser Gln Ile Pro Gln Lys Asp
                645                 650                 655

Leu Leu Glu Thr Val His Val Arg Glu Gln Gly Met Val Lys Lys Pro
                660                 665                 670

Lys Gln Glu Leu Pro Pro Leu Thr Lys Ala Glu His Ala Met Gln
            675                 680                 685

Lys Arg Ser Thr Thr Glu Leu Gly Glu Asn Leu Gln Glu Leu Arg Asp
690                 695                 700

Leu Thr Gln Glu Met Glu Val His Ala Glu Lys Leu Lys Trp Leu Asn
705                 710                 715                 720

Arg Thr Glu Leu Glu Met Leu Ser Asp Lys Ser Leu Ser Leu Pro Glu
                725                 730                 735

Arg Asp Lys Ile Ser Glu Ser Leu Arg Thr Val Asn Met Thr Trp Asn
                740                 745                 750

Lys Ile Cys Arg Glu Val Pro Thr Thr Leu Lys Glu Cys Ile Gln Glu
                755                 760                 765

Pro Ser Ser Val Ser Gln Thr Arg Ile Ala Ala His Pro Asn Val Gln
770                 775                 780

Lys Val Leu Val Ser Ser Ala Ser Asp Ile Pro Val Gln Ser His
785                 790                 795                 800

Arg Thr Ser Glu Ile Ser Ile Pro Ala Asp Leu Asp Lys Thr Ile Thr
                805                 810                 815

Glu Leu Ala Asp Trp Leu Val Leu Ile Asp Gln Met Leu Lys Ser Asn
                820                 825                 830

Ile Val Thr Val Gly Asp Val Glu Glu Ile Asn Lys Thr Val Ser Arg
                835                 840                 845

Met Lys Ile Thr Lys Ala Asp Leu Glu Gln Arg His Pro Gln Leu Asp
850                 855                 860

Tyr Val Phe Thr Leu Ala Gln Asn Leu Lys Asn Lys Ala Ser Ser Ser
865                 870                 875                 880

Asp Met Arg Thr Ala Ile Thr Glu Lys Leu Glu Arg Val Lys Asn Gln
                885                 890                 895

Trp Asp Gly Thr Gln His Gly Val Glu Leu Arg Gln Gln Leu Glu
            900                 905                 910

Asp Met Ile Ile Asp Ser Leu Gln Trp Asp Asp His Arg Glu Glu Thr
                915                 920                 925

Glu Glu Leu Met Arg Lys Tyr Glu Ala Arg Leu Tyr Ile Leu Gln Gln
930                 935                 940

Ala Arg Arg Asp Pro Leu Thr Lys Gln Ile Ser Asp Asn Gln Ile Leu
945                 950                 955                 960

Leu Gln Glu Leu Gly Pro Gly Asp Gly Ile Val Met Ala Phe Asp Asn
                965                 970                 975

Val Leu Gln Lys Leu Leu Glu Glu Tyr Gly Ser Asp Asp Thr Arg Asn
                980                 985                 990

Val Lys Glu Thr Thr Glu Tyr Leu Lys Thr Ser Trp Ile Asn Leu Lys
                995                 1000                1005

Gln Ser Ile Ala Asp Arg Gln Asn Ala Leu Glu Ala Glu Trp Arg Thr
    1010                1015                1020

Val Gln Ala Ser Arg Arg Asp Leu Glu Asn Phe Leu Lys Trp Ile Gln
1025                1030                1035                1040
```

-continued

Glu Ala Glu Thr Thr Val Asn Val Leu Val Asp Ala Ser His Arg Glu
              1045                1050                1055

Asn Ala Leu Gln Asp Ser Ile Leu Ala Arg Glu Leu Lys Gln Gln Met
              1060                1065                1070

Gln Asp Ile Gln Ala Glu Ile Asp Ala His Asn Asp Ile Phe Lys Ser
              1075                1080                1085

Ile Asp Gly Asn Arg Gln Lys Met Val Lys Ala Leu Gly Asn Ser Glu
              1090                1095                1100

Glu Ala Thr Met Leu Gln His Arg Leu Asp Asp Met Asn Gln Arg Trp
1105                1110                1115                1120

Asn Asp Leu Lys Ala Lys Ser Ala Ser Ile Arg Ala His Leu Glu Ala
              1125                1130                1135

Ser Ala Glu Lys Trp Asn Arg Leu Leu Met Ser Leu Glu Glu Leu Ile
              1140                1145                1150

Lys Trp Leu Asn Met Lys Asp Glu Glu Leu Lys Lys Gln Met Pro Ile
              1155                1160                1165

Gly Gly Asp Val Pro Ala Leu Gln Leu Gln Tyr Asp His Cys Lys Ala
              1170                1175                1180

Leu Arg Arg Glu Leu Lys Glu Lys Glu Tyr Ser Val Leu Asn Ala Val
1185                1190                1195                1200

Asp Gln Ala Arg Val Phe Leu Ala Asp Gln Pro Ile Glu Ala Pro Glu
              1205                1210                1215

Glu Pro Arg Arg Asn Leu Gln Ser Lys Thr Glu Leu Thr Pro Glu Glu
              1220                1225                1230

Arg Ala Gln Lys Ile Ala Lys Ala Met Arg Lys Gln Ser Ser Glu Val
              1235                1240                1245

Lys Glu Lys Trp Glu Ser Leu Asn Ala Val Thr Ser Asn Trp Gln Lys
              1250                1255                1260

Gln Val Asp Lys Ala Leu Glu Lys Leu Arg Asp Leu Gln Gly Ala Met
1265                1270                1275                1280

Asp Asp Leu Asp Ala Asp Met Lys Glu Ala Glu Ser Val Arg Asn Gly
              1285                1290                1295

Trp Lys Pro Val Gly Asp Leu Leu Ile Asp Ser Leu Gln Asp His Ile
              1300                1305                1310

Glu Lys Ile Met Ala Phe Arg Glu Glu Ile Ala Pro Ile Asn Phe Lys
              1315                1320                1325

Val Lys Thr Val Asn Asp Leu Ser Ser Gln Leu Ser Pro Leu Asp Leu
              1330                1335                1340

His Pro Ser Leu Lys Met Ser Arg Gln Leu Asp Asp Leu Asn Met Arg
1345                1350                1355                1360

Trp Lys Leu Leu Gln Val Ser Val Asp Asp Arg Leu Lys Gln Leu Gln
              1365                1370                1375

Glu Ala His Arg Asp Phe Gly Pro Ser Ser Gln His Phe Leu Ser Thr
              1380                1385                1390

Ser Val Gln Leu Pro Trp Gln Arg Ser Ile Ser His Asn Lys Val Pro
              1395                1400                1405

Tyr Tyr Ile Asn His Gln Thr Gln Thr Thr Cys Trp Asp His Pro Lys
              1410                1415                1420

Met Thr Glu Leu Phe Gln Ser Leu Ala Asp Leu Asn Asn Val Arg Phe
1425                1430                1435                1440

Ser Ala Tyr Arg Thr Ala Ile Lys Ile Arg Arg Leu Gln Lys Ala Leu
              1445                1450                1455

-continued

Cys Leu Asp Leu Leu Glu Leu Ser Thr Thr Asn Glu Ile Phe Lys Gln
            1460                1465                1470

His Lys Leu Asn Gln Asn Asp Gln Leu Leu Ser Val Pro Asp Val Ile
        1475                1480                1485

Asn Cys Leu Thr Thr Thr Tyr Asp Gly Leu Glu Gln Met His Lys Asp
    1490                1495                1500

Leu Val Asn Val Pro Leu Cys Val Asp Met Cys Leu Asn Trp Leu Leu
1505                1510                1515                1520

Asn Val Tyr Asp Thr Gly Arg Thr Gly Lys Ile Arg Val Gln Ser Leu
            1525                1530                1535

Lys Ile Gly Leu Met Ser Leu Ser Lys Gly Leu Leu Glu Glu Lys Tyr
        1540                1545                1550

Arg Tyr Leu Phe Lys Glu Val Ala Gly Pro Thr Glu Met Cys Asp Gln
    1555                1560                1565

Arg Gln Leu Gly Leu Leu His Asp Ala Ile Gln Ile Pro Arg Gln
    1570                1575                1580

Leu Gly Glu Val Ala Ala Phe Gly Gly Ser Asn Ile Glu Pro Ser Val
1585                1590                1595                1600

Arg Ser Cys Phe Gln Gln Asn Asn Asn Lys Pro Glu Ile Ser Val Lys
            1605                1610                1615

Glu Phe Ile Asp Trp Met His Leu Glu Pro Gln Ser Met Val Trp Leu
        1620                1625                1630

Pro Val Leu His Arg Val Ala Ala Ala Glu Thr Ala Lys His Gln Ala
    1635                1640                1645

Lys Cys Asn Ile Cys Lys Glu Cys Pro Ile Val Gly Phe Arg Tyr Arg
    1650                1655                1660

Ser Leu Lys His Phe Asn Tyr Asp Val Cys Gln Ser Cys Phe Phe Ser
1665                1670                1675                1680

Gly Arg Thr Ala Lys Gly His Lys Leu His Tyr Pro Met Val Glu Tyr
            1685                1690                1695

Cys Ile Pro Thr Thr Ser Gly Glu Asp Val Arg Asp Phe Thr Lys Val
        1700                1705                1710

Leu Lys Asn Lys Phe Arg Ser Lys Lys Tyr Phe Ala Lys His Pro Arg
    1715                1720                1725

Leu Gly Tyr Leu Pro Val Gln Thr Val Leu Glu Gly Asp Asn Leu Glu
    1730                1735                1740

Thr Pro Ile Thr Leu Ile Ser Met Trp Pro Glu His Tyr Asp Pro Ser
1745                1750                1755                1760

Gln Ser Pro Gln Leu Phe His Asp Asp Thr His Ser Arg Ile Glu Gln
            1765                1770                1775

Tyr Ala Thr Arg Leu Ala Gln Met Glu Arg Thr Asn Gly Ser Phe Leu
        1780                1785                1790

Thr Asp Ser Ser Ser Thr Thr Gly Ser Val Glu Asp Glu His Ala Leu
    1795                1800                1805

Ile Gln Gln Tyr Cys Gln Thr Leu Gly Gly Glu Ser Pro Val Ser Gln
    1810                1815                1820

Pro Gln Ser Pro Ala Gln Ile Leu Lys Ser Val Glu Arg Glu Glu Arg
1825                1830                1835                1840

Gly Glu Leu Glu Arg Ile Ile Ala Asp Leu Glu Glu Glu Gln Arg Asn
            1845                1850                1855

Leu Gln Val Glu Tyr Glu Gln Leu Lys Asp Gln His Leu Arg Arg Gly
        1860                1865                1870

Leu Pro Val Gly Ser Pro Pro Glu Ser Ile Ile Ser Pro His His Thr

-continued

```
              1875                1880                1885

Ser Glu Asp Ser Glu Leu Ile Ala Glu Ala Lys Leu Leu Arg Gln His
    1890                1895                1900

Lys Gly Arg Leu Glu Ala Arg Met Gln Ile Leu Glu Asp His Asn Lys
1905                1910                1915                1920

Gln Leu Glu Ser Gln Leu His Arg Leu Arg Gln Leu Leu Glu Gln Pro
              1925                1930                1935

Glu Ser Asp Ser Arg Ile Asn Gly Val Ser Pro Trp Ala Ser Pro Gln
        1940                1945                1950

His Ser Ala Leu Ser Tyr Ser Leu Asp Pro Asp Ala Ser Gly Pro Gln
        1955                1960                1965

Phe His Gln Ala Ala Gly Glu Asp Leu Leu Ala Pro Pro His Asp Thr
    1970                1975                1980

Ser Thr Asp Leu Thr Glu Val Met Glu Gln Ile His Ser Thr Phe Pro
1985                1990                1995                2000

Ser Cys Cys Pro Asn Val Pro Ser Arg Pro Gln Ala Met
              2005                2010

<210> SEQ ID NO 10
<211> LENGTH: 25
<212> TYPE: DNA
<213> ORGANISM: Homo sapiens

<400> SEQUENCE: 10
acaggacatc ccagtgtgca gttcg                                          25

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Sequence
      obtainable from non-human mammal

<400> SEQUENCE: 11
gattgtggat gaaaacagtg gg                                             22

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
gatgttcctg tgaggccttc gag                                            23

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
cactcttgga aaatcgagcg t                                              21

<210> SEQ ID NO 14
<211> LENGTH: 22
<212> TYPE: DNA
```

```
<213> ORGANISM: Artificial Sequence
<220> FEATURE:
<223> OTHER INFORMATION: Description of Artificial Sequence:
      Oligonucleotide

<400> SEQUENCE: 14
actatgatgt ctgccagagt tg                                        22

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
gatccaatag cttccttcca tcttt                                     25

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
tggaaaaagt ggaggttgga                                           20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
tccaacctcc acttttttcca                                          20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
gcctggagag ctacatgccc t                                         21

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
ctccacatct ttttcctcat catct                                     25

<210> SEQ ID NO 20
<211> LENGTH: 22
<212> TYPE: DNA
<213> ORGANISM: Artificial Sequence
```

```
<220> FEATURE:
<223> OTHER INFORMATION: Description of Artificial Sequence:
      Oligonucleotide

<400> SEQUENCE: 20
gattgtggtg atggttgtag aa                                             22

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
gatgatgagg aaaaagatgt ggag                                           24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
aaacccaaaa taacacagga catc                                           24

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
agtgtaactt ctctctggtg                                                20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
taagcagatg taggtgatga gc                                             22

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
gctgcttttg ttgtccactt c                                              21

<210> SEQ ID NO 26
<211> LENGTH: 22
<212> TYPE: DNA
<213> ORGANISM: Artificial Sequence
<220> FEATURE:
```

```
<223> OTHER INFORMATION: Description of Artificial Sequence:
      Oligonucleotide

<400> SEQUENCE: 26
atagcttcct tccatctttg ag                                              22

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 27
ctccacgttc ttccctctct act                                             23

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 28
gcgtgcagtg gaccattttt cagattta                                        28

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 29
cgctgcagca gccaccacat ttcgttg                                         27

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 30
gcgtgcagat cgagcgttta tccatttg                                        28
```